(12) United States Patent
Rosenberg et al.

(10) Patent No.: US 8,431,079 B2
(45) Date of Patent: Apr. 30, 2013

(54) ANALYZER FOR PERFORMING MEDICAL DIAGNOSTIC ANALYSIS

(75) Inventors: Burkard Rosenberg, Horw (CH); Juergen Rauh, Mellingen (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/956,303

(22) Filed: Nov. 30, 2010

(65) Prior Publication Data

US 2011/0293475 A1    Dec. 1, 2011

Related U.S. Application Data

(63) Continuation of application No. PCT/EP2009/003796, filed on May 28, 2009.

(30) Foreign Application Priority Data

May 30, 2008    (EP) .................................... 08009896

(51) Int. Cl.
*G01N 35/04* (2006.01)
*G01N 35/10* (2006.01)

(52) U.S. Cl.
USPC ................. 422/64; 422/63; 436/47; 436/48; 436/49

(58) Field of Classification Search .......................... None
See application file for complete search history.

(56) References Cited

U.S. PATENT DOCUMENTS

| | | | |
|---|---|---|---|
| 4,054,416 A | | 10/1977 | Duff |
| 4,338,279 A | * | 7/1982 | Orimo et al. ..................... 422/64 |
| 5,233,844 A | * | 8/1993 | Knippscheer et al. .......... 62/440 |
| 5,419,871 A | * | 5/1995 | Muszak et al. .................. 422/63 |
| 5,985,672 A | | 11/1999 | Kegelman et al. |
| 6,106,781 A | | 8/2000 | Rosenberg |
| 6,375,898 B1 | * | 4/2002 | Ulrich .............................. 422/64 |
| 2004/0131499 A1 | | 7/2004 | Okada et al. |
| 2006/0159587 A1 | | 7/2006 | Fechtner et al. |

FOREIGN PATENT DOCUMENTS

| | | |
|---|---|---|
| EP | 0 576 291 A2 | 6/1993 |
| EP | 1 906 187 A1 | 7/2002 |
| EP | 1 870 713 A1 | 4/2006 |
| JP | 2-071155 A | 3/1990 |
| JP | 2011-509635 A | 3/2011 |
| WO | 02/18956 A2 | 3/2002 |

OTHER PUBLICATIONS

International Search Report, Appl. No. PCT/EP2009/003796, Aug. 17, 2009, 4 pages.

* cited by examiner

*Primary Examiner* — Kathryn Wright
(74) *Attorney, Agent, or Firm* — Dinsmore & Shohl LLP

(57) ABSTRACT

Embodiments of an analyzer for performing medical diagnostic analysis of biological samples are disclosed. In one embodiment, the analyzer may have a first and at least a second disk-shaped cuvette conveyor each having an array of cuvette holders, a first drive unit for rotating the first cuvette conveyor about a rotation axis, and a second drive unit for rotating the second cuvette conveyor about the rotation axis. The operation of the second drive unit is independent from the operation of the first drive unit. The first cuvette conveyor and the second cuvette conveyor are spaced from each other in an axial direction along the rotation axis and with an air gap between them. The cuvette holders of the first cuvette conveyor and the cuvette holders of the second cuvette conveyor are adapted for holding cuvettes having the same shape and dimensions.

12 Claims, 26 Drawing Sheets

ANALYZER FOR PERFORMING MEDICAL DIAGNOSTIC ANALYSIS

CROSS REFERENCE TO RELATED APPLICATIONS

This application is a continuation of PCT Application No. EP2009/003796, filed May 28, 2009, which claims priority to European application No. 08009896.5, filed May 30, 2008.

TECHNICAL FIELD

The present disclosure concerns an analyzer for performing medical diagnostic analysis of biological samples.

BACKGROUND

In the prior art there is known a conveying system for analytical samples which comprises a disk-shaped cuvette conveyor and drive unit. The cuvette conveyor has an array of cuvette holders located at the periphery of the cuvette conveyor and uniformly spaced along a first circle. The drive unit rotates the cuvette conveyor about a rotation axis in order to position each of the cuvettes carried by the cuvette conveyor at an angular position.

However, such a conveyor comprises 99 cuvette holders. This number limits the number of samples that can be analyzed by the analyzer per unit of time. Such an analyzer is used preferably for clinical chemistry tests only, because for immunoassays the maximum number of samples that can be analyzed by the analyzer per unit of time would be even lower. Additionally, immunoassays require different dilution steps and/or incubation times, compared to clinical chemistry assays.

SUMMARY

As discussed herein, embodiments of an analyzer for performing medical diagnostic analysis of biological samples are disclosed. In one embodiment, for example, the analyzer may comprise a first disk-shaped cuvette conveyor having a first array of cuvette holders spaced along a first circle; a first drive unit which rotates the first cuvette conveyor about a rotation axis in order to position cuvettes carried by the first cuvette conveyor at a first angular position; and at least a second disk-shaped cuvette conveyor having a second array of cuvette holders spaced along a second circle. The cuvette holders of the first cuvette conveyor and the cuvette holders of the at least second cuvette conveyor hold cuvettes having the same shape and dimensions. The centers of the first circle and the second circle lie on a vertical axis, which is a common rotation axis of the first cuvette conveyor and the at least second cuvette conveyor. The first cuvette conveyor and the at least second cuvette conveyor are rotatable around the common rotation axis, and the first cuvette conveyor and the at least second cuvette conveyor are spaced from each other in an axial direction along the rotation axis and with an air gap between the first cuvette conveyor and the at least second cuvette conveyor. The analyzer may also comprise at least a second drive unit which rotates the at least second cuvette conveyor about the vertical rotation axis in order to position cuvettes carried by the at least second cuvette conveyor at a second angular position, and in which the operation of the at least second drive unit is independent from the operation of the first drive unit.

The subject invention will now be described in terms of its preferred embodiments with reference to the accompanying drawings. These embodiments are set forth to aid the understanding of the invention, but are not to be construed as limiting.

Figure 1:
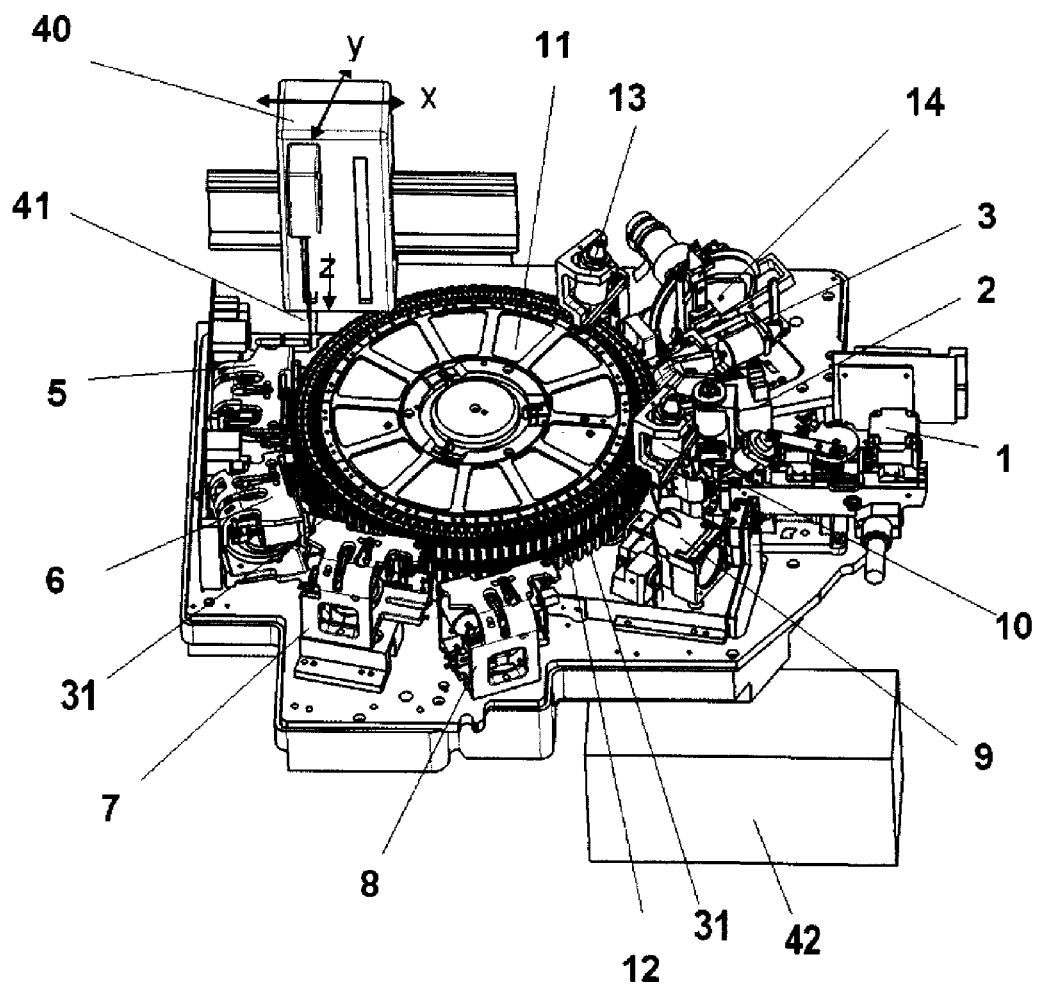
FIG. 1 shows a first perspective view of some components of an analyzer according to the invention.

REFERENCE NUMERALS USED IN DRAWINGS 1 workstation WSA
2 fluorescence polarization photometer
3 workstation WSE
4 cuvette conveyor
5 workstation WSB
6 workstation WS2
7 workstation WSC1
8 workstation WSC2
9 absorption photometer
10 first waste drop-off station
11 second cuvette conveyor/upper cuvette conveyor
12 first cuvette conveyor/lower cuvette conveyor
13 second waste drop-off station
14 workstation WSF
15 analyzer housing without cover part thereof
16 opening for pipetting reagents at workstation 5 (WSB)
17 opening for pipetting reagents at workstation 6 (WS2)
18 opening for pipetting samples at workstation 7 (WSC1)
19 opening for pipetting samples at workstation 8 (WSC2)
20 fan
21 heating element
22 workstation WSK
23 workstation WSL
24 conveyor drive for first cuvette conveyor 12
25 conveyor drive for second cuvette conveyor 11
26 workstation WSI 1
27 workstation WSI 2
28 workstation WSG
29 workstation WSH
31 reaction cuvette
32 body of cuvette 31
33 lower end portion of cuvette 31
34 upper end portion of cuvette 31
35 bottom wall of cuvette 31
36 opening of cuvette 31
37 tongue
38 tongue
39 length symmetry axis of cuvette 31
40 pipetting head
41 pipetting needle
42 control unit
43 rotation axis
44 pipetting position in working station 14 (WSF)
45 pipetting position in working station 28 (WSG)
46 pipetting position in working station 29 (WSH)
47 planar side wall of the cuvette 31
48 planar side wall of the cuvette 31

DETAILED DESCRIPTION

Within the context of the instant invention, the cuvettes are containers for holding samples and/or mixing samples with reagents. According to one embodiment, cuvettes are adapted to allow optical detection of the liquid contained therein directly through the cuvette walls.

The embodiments of the present invention make it possible to achieve a higher number of samples analyzed per unit of time and/or to perform clinical chemistry tests as well as immunoassays using the same analyzer. Moreover, due to the fact that the at least two cuvette conveyors can operate synergistically, e.g. by exchanging cuvettes and/or delegating assay steps to the other while one is busy with other operations, or when failure in one occurs, time, costs and space can be saved if compared to e.g. two analyzers each carrying only one cuvette conveyor. Accordingly, the embodiments of the invention overcome the limitation mentioned above in the background at least by disclosing an analyzer that per unit of time can analyze a higher number of samples.

Various illustrated embodiments of the invention are described hereinafter with reference to the accompanying drawings.

EXAMPLES

Example 1

First Illustrated Embodiment of an Analyzer

Figure 4:
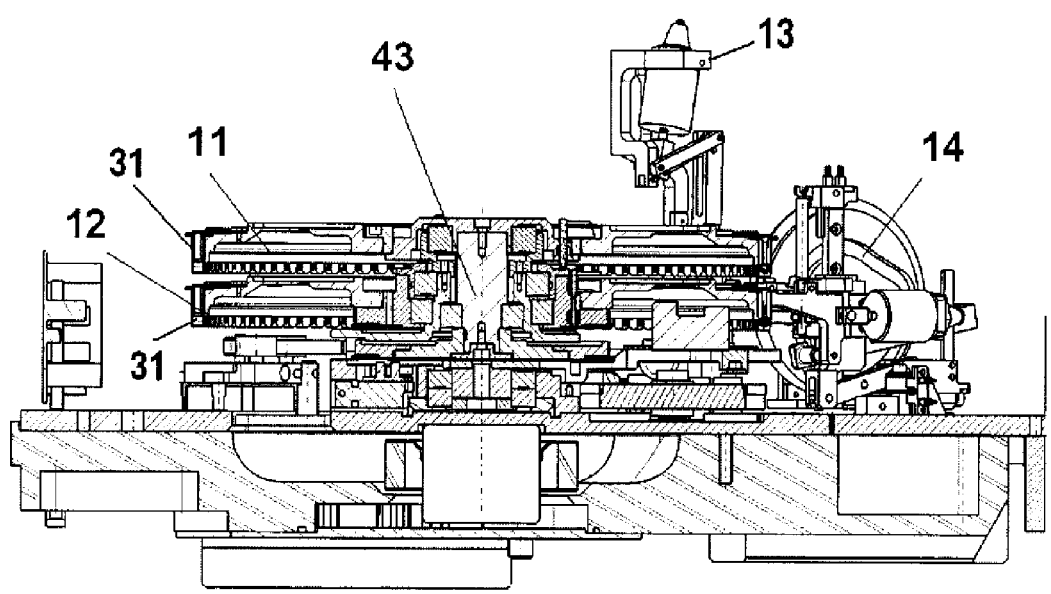
FIG. 4 shows a cross-sectional view taken along a plane A-A in FIG. 3.
Figure 14:
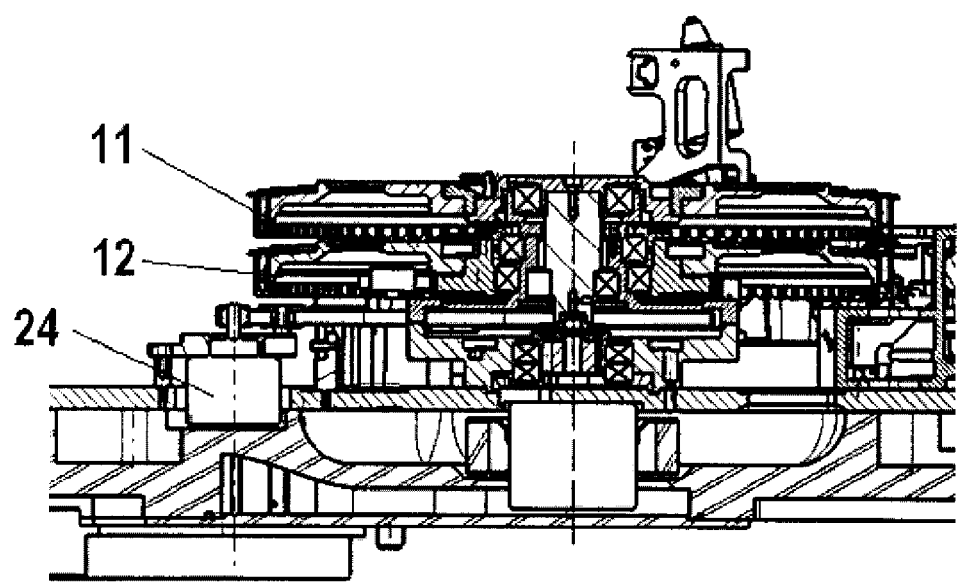
FIG. 14 shows a cross-sectional view of a conveyor drive 24 represented in FIG. 13 taken along plane E-E in FIG. 13.

FIG. 1 shows an analyzer for performing medical diagnostic analysis of biological samples comprising the following components: a first disk-shaped cuvette conveyor 12, and first drive unit 24 (not shown in FIG. 1, but shown in FIG. 14) for rotating the first cuvette conveyor 12 about a rotation axis 43 (represented in FIG. 4). Rotation axis 43 passes through the center of cuvette conveyor 12 and extends in vertical direction, e.g. in Z-direction in FIG. 1.

Cuvette conveyor 12 is arranged parallel to a horizontal plane, e.g. an X-Y-plane in FIG. 1, and has a first array of cuvette holding positions, hereinafter called cuvette holders, spaced along a first circle the center of which lies on rotation axis 43.

First drive unit 24 rotate cuvette conveyor 12 about the vertical rotation axis 43 in order to position cuvettes 31 carried by the first cuvette conveyor at a first angular position.

Figure 15:
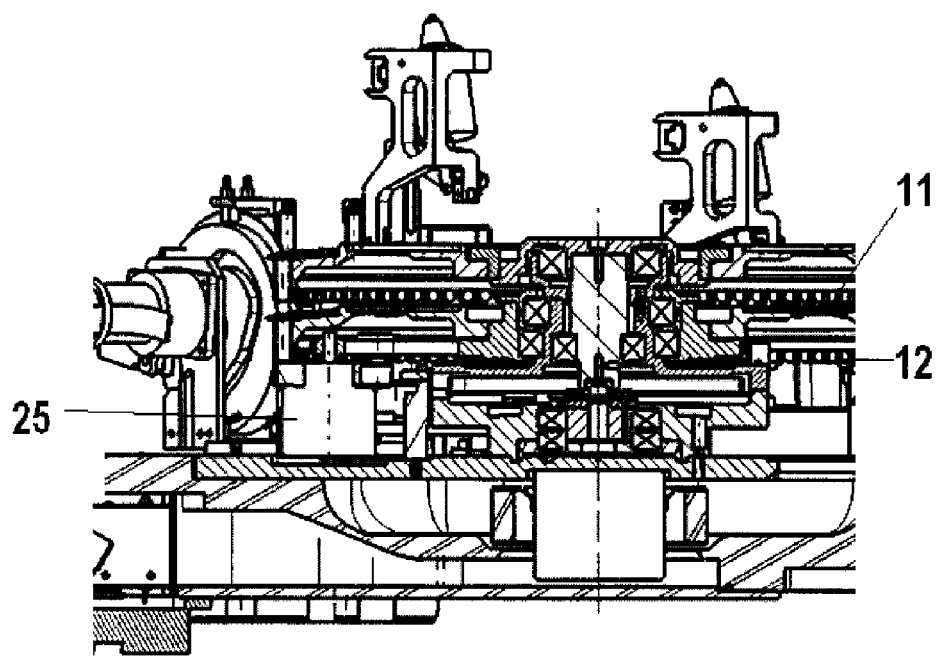
FIG. 15 shows a cross-sectional view of conveyor drive 25 represented in FIG. 13 taken along plane F-F in FIG. 14.

The analyzer shown by FIG. 1 further comprises: at least a second disk-shaped cuvette conveyor 11, and at least second drive unit 25 (not shown in FIG. 1, but shown by FIG. 15). The second drive unit rotates the at least second cuvette conveyor 11 about vertical rotation axis 43 in order to position cuvettes 31, carried by the at least second cuvette conveyor 11, at a second angular position. The operation of the at least second drive unit 25 is independent from the operation of the first drive unit 24.

Cuvette conveyor 11 is also arranged parallel to a horizontal plane, e.g. an X-Y-plane in FIG. 1, and has a second array of cuvette holders spaced along a second circle the center of which also lies on rotation axis 43.

The cuvette holders of the first cuvette conveyor 12 and the cuvette holders of the at least second cuvette conveyor 11 are adapted for holding cuvettes 31, which in one embodiment have the same shape and dimensions.

The centers of the first circle and of the second circle lie on a vertical axis which is a common rotation axis 43 of the first cuvette conveyor 12 and the at least second cuvette conveyor 11.

The first cuvette conveyor 12 and the at least second cuvette conveyor 11 are rotatable around their common rotation axis 43.

The first cuvette conveyor 12 and the at least second cuvette conveyor 11 are spaced from each other in axial direction along the rotation axis 43 with an air gap between the first cuvette conveyor 12 and the at least second cuvette conveyor 11.

The analyzer shown by FIG. 1 further comprises a workstation 1 (WSA), a fluorescence polarization photometer 2, a workstation 3 (WSE), a workstation 5 (WSB), a workstation 6 (WS2), a workstation 7 (WSC1), a workstation 8 (WSC2), absorption photometer 9, a first waste drop-off station 10, an automatic pipetting unit 40 and a control unit 42.

The analyzer shown by FIG. 1 in another embodiment may comprise a second waste drop-off station 13.

Workstation 1 (WSA) transports a cuvette and positions it in a cuvette holder of conveyor 12 and after termination of the processing of the cuvette removes it from conveyor 12 and brings it to a waste drop-off station 10 which delivers the cuvette to a waste container.

Fluorescence polarization photometer 2 measures the content of a liquid, e.g. comprising a blood sample, contained in a cuvette.

Workstation 3 (WSE) takes a selected cuvette containing a liquid comprising a sample, e.g. a blood sample, from conveyor 12, transports it to fluorescence polarization photometer 2, and brings the cuvette back to a cuvette holder of conveyor 12.

Workstation 5 (WSB) takes a selected cuvette containing a liquid from conveyor 12, brings it to a reagent pipetting position 16 where a first reagent is pipetted into the cuvette, agitates the cuvette for effective mixing of the liquids in the cuvette, and after this mixing step brings the cuvette back to a cuvette holder of conveyor 12.

Workstation 6 (WS2) takes a selected cuvette containing a liquid from conveyor 12, brings it to a reagent pipetting position 17 where a second reagent is pipetted into the cuvette, agitates the cuvette for effective mixing of the liquids in the cuvette, and after this mixing step brings the cuvette back to a cuvette holder of conveyor 12.

Workstation 7 (WSC1) takes a selected cuvette containing a liquid from conveyor 12, brings it to a reagent pipetting position 18 where a liquid, e.g. sample, reagent or a dilution liquid is pipetted into the cuvette, agitates the cuvette for effective mixing of the liquids in the cuvette, and after this mixing step brings the cuvette back to a cuvette holder of conveyor 12.

Workstation 8 (WSC2) takes a selected cuvette containing a liquid from conveyor 12, brings it to a reagent pipetting position 19 where a liquid, e.g. sample, reagent or a dilution liquid is pipetted into the cuvette, agitates the cuvette for effective mixing of the liquids in the cuvette, and after this mixing step brings the cuvette back to a cuvette holder of conveyor 12.

In another embodiment of the analyzer shown by FIG. 1, Workstation 7 (WSC1) takes a selected cuvette containing a liquid from conveyor 11, brings it to a reagent pipetting position 18 where a liquid, e.g. sample, reagent or a dilution liquid is pipetted into the cuvette, agitates the cuvette for effective mixing of the liquids in the cuvette, and after this mixing step brings the cuvette back to a cuvette holder of conveyor 11.

Absorption photometer 9 measures the content of a liquid, e.g. comprising a blood sample, contained in a cuvette.

The cuvette holders of the first cuvette conveyor 12 and the cuvette holders of the at least second cuvette conveyor 11 are adapted for holding cuvettes 31 having an inner volume in a range going from 0.2 to 3 milliliter.

Figure 2:
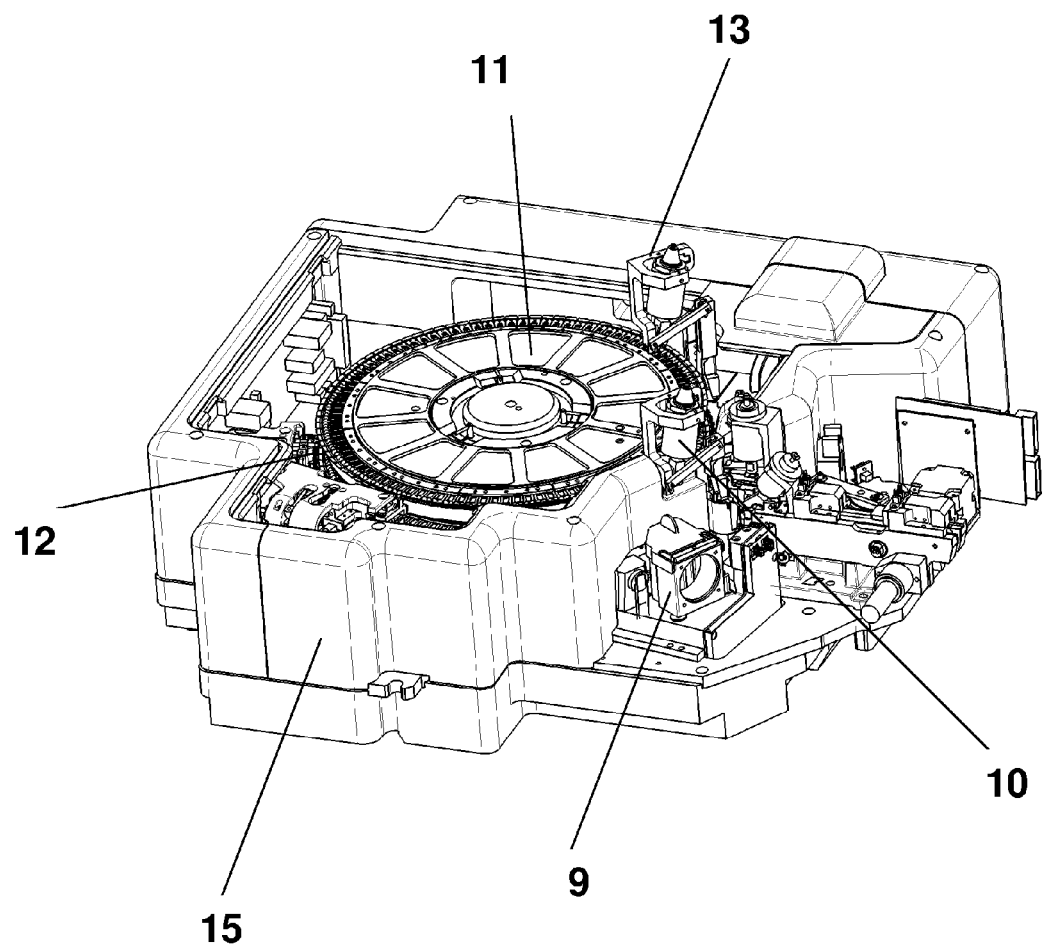
FIG. 2 shows a perspective view of some components of an analyzer according to the invention similar to FIG. 1 comprising a housing of this analyzer open from the top.

As shown by FIG. 2, another embodiment of the analyzer shown by FIG. 1 further comprises a housing 15 the interior of which defines a chamber. This chamber has an upper opening which is closed by a removable cover (not shown) during operation of the analyzer. That opening allows access to the components contained therein.

Figure 7:
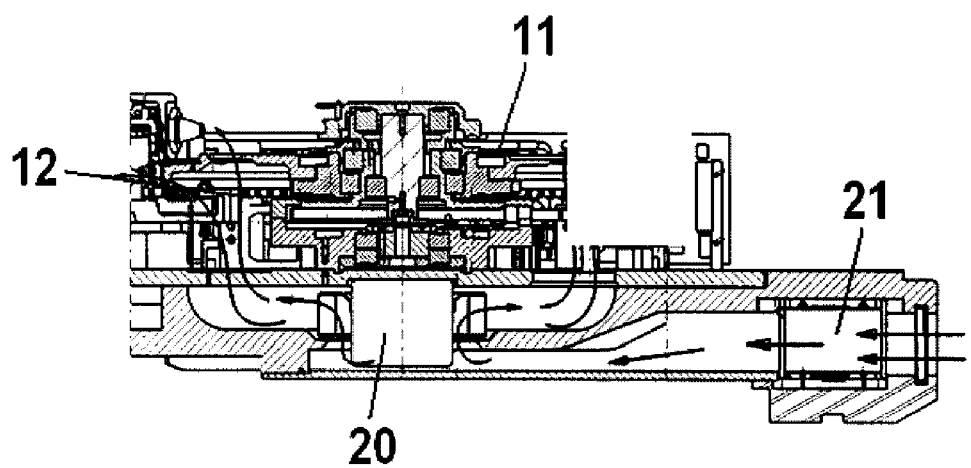
FIG. 7 shows a cross-sectional view taken along planes D-D represented in FIG. 6.

During operation of the analyzer and with the above mentioned chamber closed by the above mentioned cover, air temperature within the chamber is regulated and maintained at a determined value by means of a temperature regulation arrangement which includes a fan 20 and a heating element 21 shown by FIG. 7. In FIG. 7 the air flow generated by fan 20 is represented by arrows. The first cuvette conveyor 12 and the at least second cuvette conveyor 11 are located within the above mentioned chamber of housing 15 and are thereby kept at the same temperature.

Figure 5:
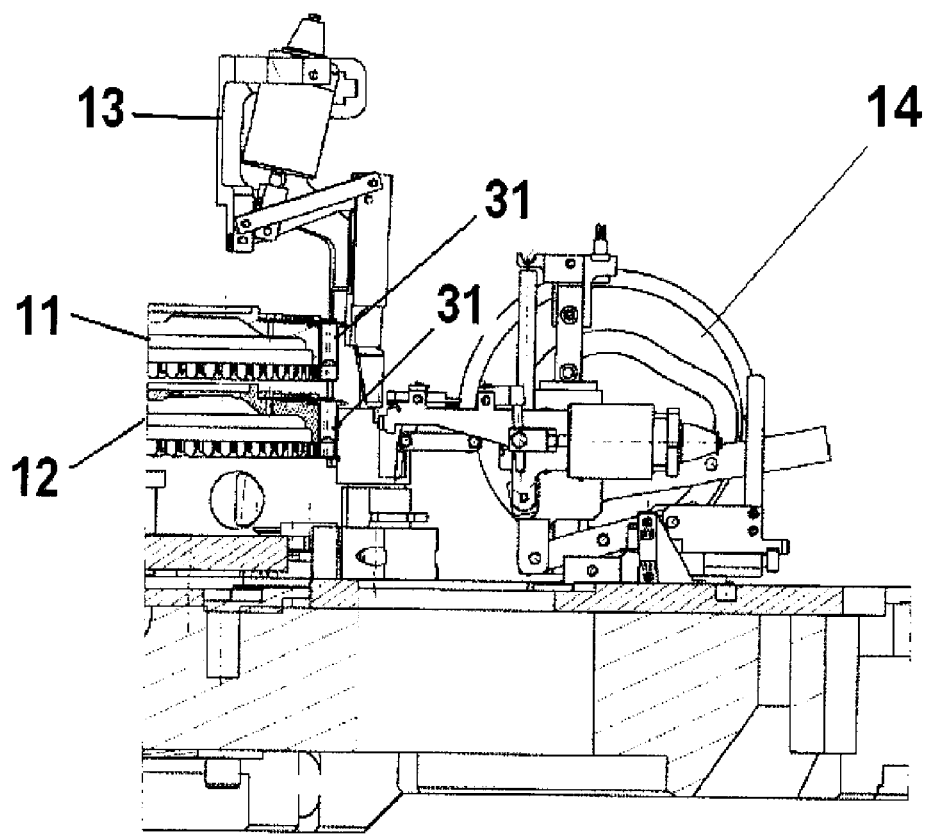
FIG. 5 shows a cross-sectional view taken along a plane B-B in FIG. 3.
Figure 6:
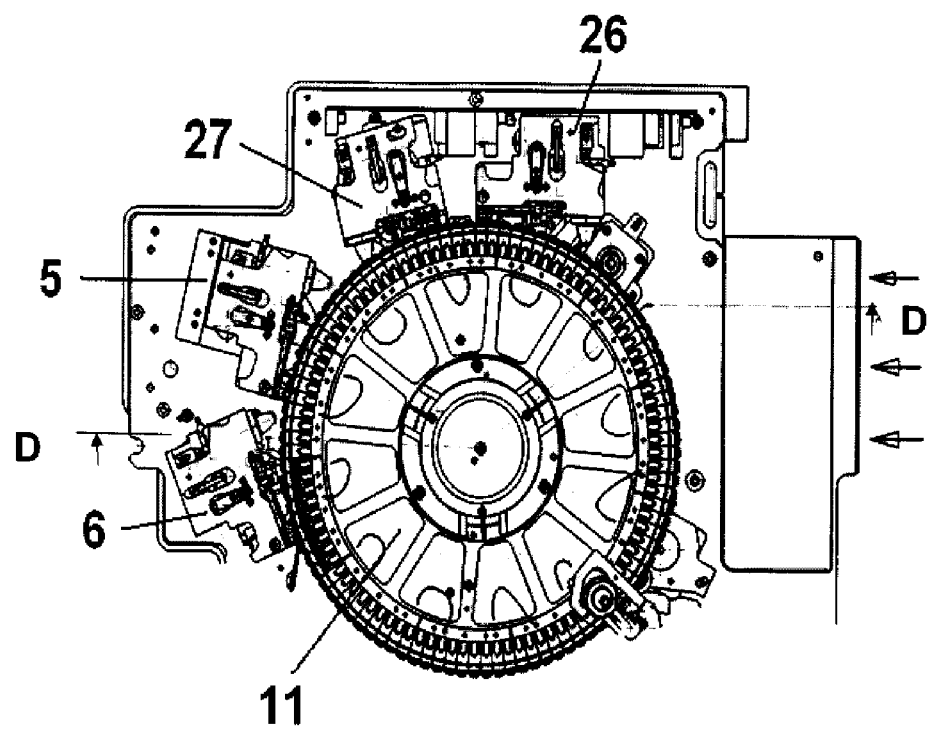
FIG. 6 shows a top plan view of some components of an analyzer according to the invention as represented in FIG. 1.
Figure 8:
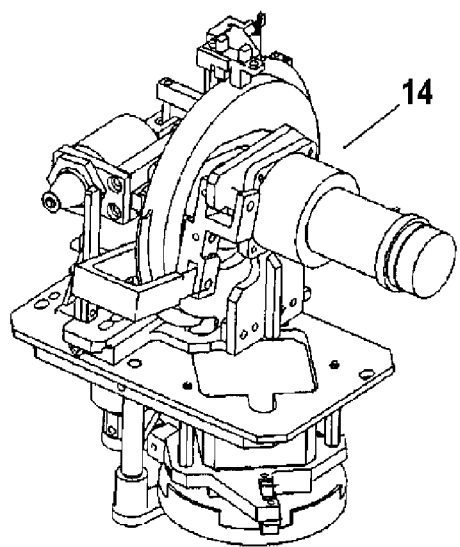
FIG. 8 shows a first perspective view of workstation 14 represented in FIG. 1.
Figure 9:
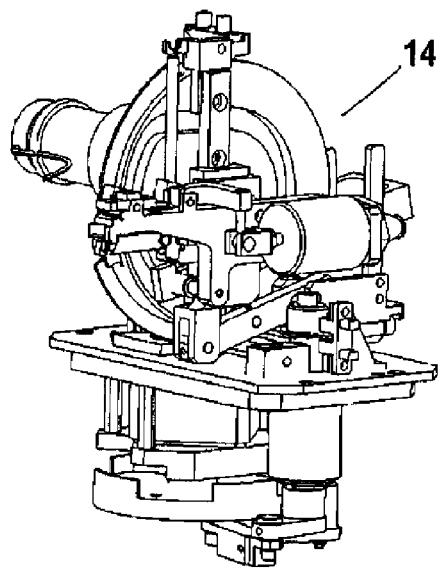
FIG. 9 shows a second perspective view of workstation 14 represented in FIG. 1.
Figure 10:
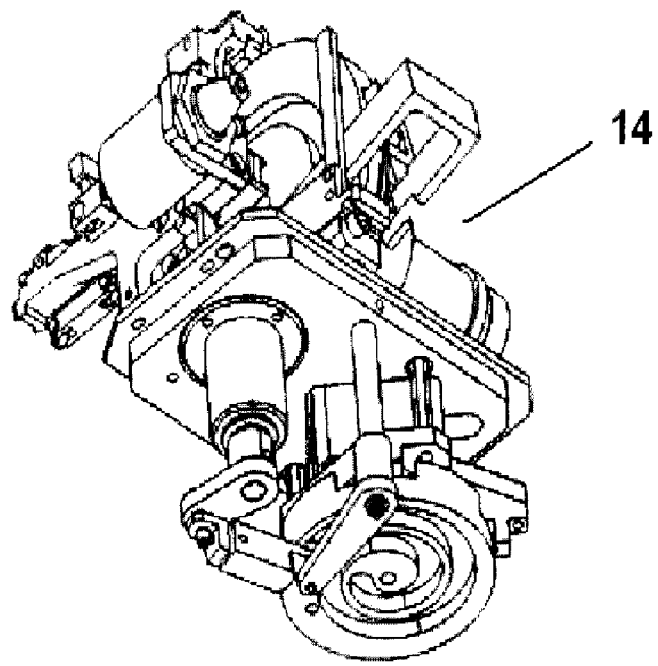
FIG. 10 shows a third perspective view of workstation 14 represented in FIG. 1.
Figure 11:
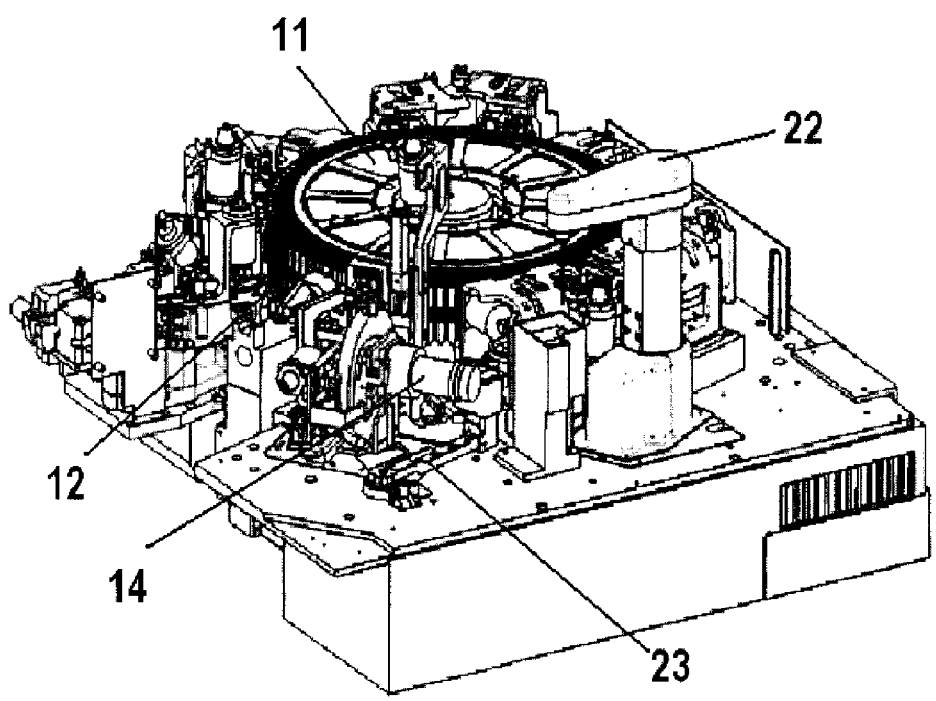
FIG. 11 shows a second perspective view of the analyzer represented in FIG. 1.
Figure 12:
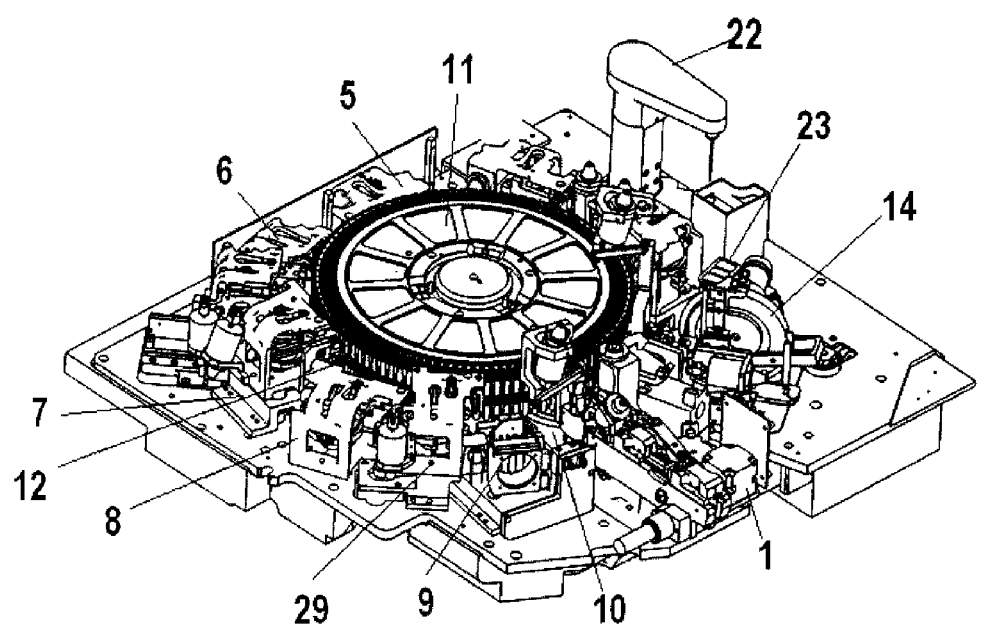
FIG. 12 shows a third perspective view of the analyzer represented in FIG. 1.
Figure 13:
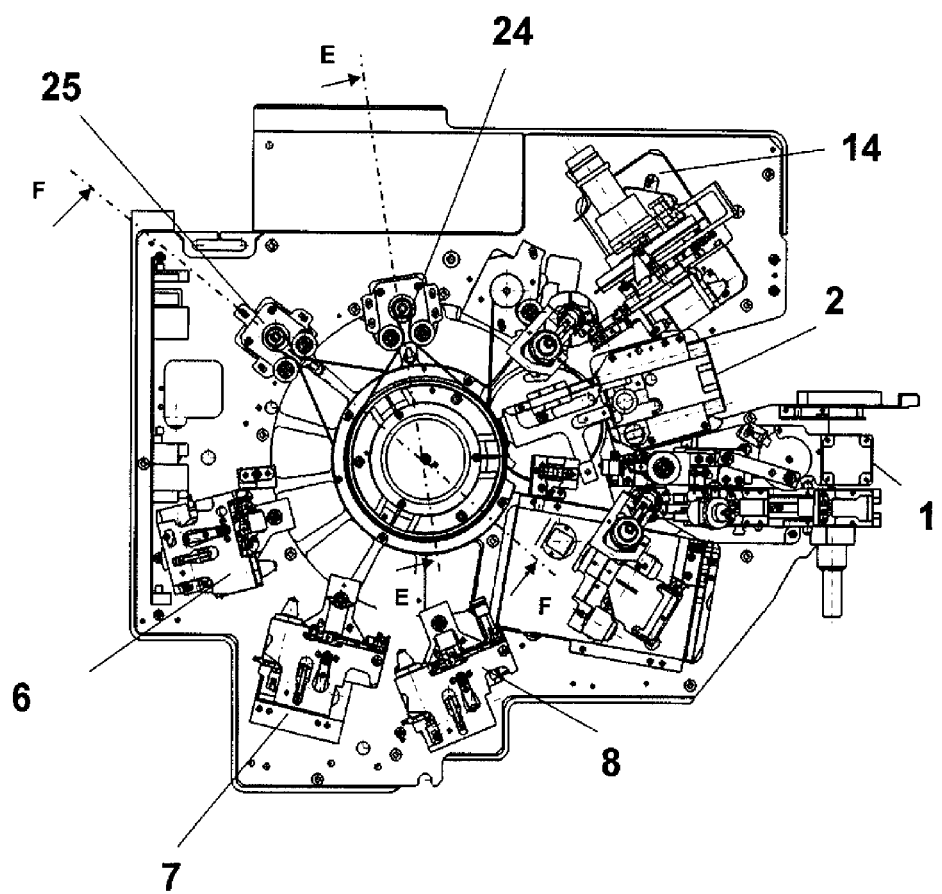
FIG. 13 shows a top plan view of some components of an analyzer according to the invention as represented in FIG. 1 without the rotatable conveyors 11 and 12, but showing the conveyor drives 24 and 25.

As shown by FIGS. 1, 4 and 5, another embodiment of the analyzer shown by FIG. 1 further comprises a first cuvette transport device 14 (WSF). The first cuvette transport device 14 is located close to the periphery of the first cuvette conveyor 12, and respectively to the at least second cuvette conveyor 11. The first cuvette transport device 14 is adapted for transporting a cuvette 31 from one of the cuvette holders of the first cuvette conveyor 12 to one of the cuvette holders of the at least second cuvette conveyor 11 and/or vice versa. FIGS. 8, 9 and 10 each show a different perspective view of workstation 14 (WSF).

Other embodiments of the analyzer shown by FIG. 1 further comprise a plurality of workstations arranged around and close to the periphery of the first cuvette conveyor 12 and the at least second cuvette conveyor 11. Those workstations comprise cuvette transport device for removing a cuvette 31 from one of the cuvette holders of the first cuvette conveyor or of the at least second cuvette conveyor 11, for transporting the cuvette to a processing position, and for transporting the cuvette from the processing position to another one of the cuvette holders of the first cuvette conveyor 12 or of the at least second cuvette conveyor 11, or for transferring said cuvette 31 to a cuvette ejection device, e.g. waste drop-off station 10 or 13.

The automatic pipetting unit of the analyzer shown by FIG. 1 comprises a pipetting head 40 which transports a pipetting needle 41 in three orthogonal directions X, Y and Z for performing pipetting operations, e.g. for pipetting a sample or a reagent aliquot into a selected cuvette 31 at a selected processing position at a selected point of time. The location of the processing position is associated with the position of one of the plurality of workstations.

The control unit 42 of the analyzer shown by FIG. 1 controls the operation of the first drive unit 24, of the at least second drive unit 25, of the first cuvette transport device (WSF), of the plurality of workstations, of the automatic pipetting unit, and of the photometers 2 and 9. During operation of the analyzer, the control unit 42 continuously receives and stores the current position of each cuvette, wherein the cuvettes 31 have a variable position.

The control unit 42 controls the processing of each sample contained in one of the cuvettes 31 according to predetermined specific sequence of process steps for the treatment of that sample.

The control unit 42 optimizes the execution of the sequences of the process steps for processing the samples contained in all the cuvettes 31 and thereby maximizes the number of samples analyzed per unit of time.

In one embodiment, the at least second cuvette conveyor 11 has the same shape and dimensions as the first cuvette conveyor 12.

In another embodiment, each of the cuvette holders has a recess for receiving a tongue 37, 38 which is an integral portion of a cuvette 31. That recess extends in radial direction and the tongue 37, 38 is insertable in the recess in radial direction.

In another embodiment, the first drive unit 24 and the at least second drive unit 25 are each adapted for rotating the first cuvette conveyor 12 respectively the at least second cuvette conveyor 11 in a first sense and/or in a second sense opposite to the first sense.

In another embodiment, the first cuvette transport device 14 (WSF) is further adapted for removing a cuvette 31 from one of the cuvette holders of the at least second cuvette conveyor 11 and for transferring the cuvette 31 to a cuvette ejection device, e.g. waste drop-off station 13.

In one embodiment, the first cuvette transport device (WSF) is further adapted for transferring the cuvette 31 from one of the cuvette holders of the at least second cuvette conveyor 11 to a processing position, e.g. a pipetting position 44, and from the processing position back to the cuvette holder, or to a cuvette ejection position in waste drop-off station 13 which delivers the cuvette to a waste container.

In another embodiment, the analyzer further comprises a second cuvette transport device 1 (WSA) for automatically loading empty cuvettes 31 onto the first cuvette conveyor 12, by inserting each cuvette 31 into a cuvette holder of the first cuvette conveyor 12.

In another embodiment, the second cuvette transport device 1 (WSA) is also adapted for removing a cuvette 31 from one of the cuvette holders of the first cuvette conveyor 12 and for transferring the cuvette 31 to a cuvette ejection device, e.g. waste drop-off station 10.

In another embodiment, the second cuvette transport device 1 (WSA) is also adapted for removing a cuvette 31 from one of the cuvette holders of the at least second cuvette conveyor 12 and for transferring the cuvette 31 to a cuvette ejection device, e.g. waste drop-off station 10 or 13.

In another embodiment, the analyzer further comprises a third cuvette transport device 1 (WSA) for automatically loading empty cuvettes 31 onto the at least second cuvette conveyor 11, by inserting each cuvette 31 into a cuvette holder of the at least second cuvette conveyor 11.

Figure 3:
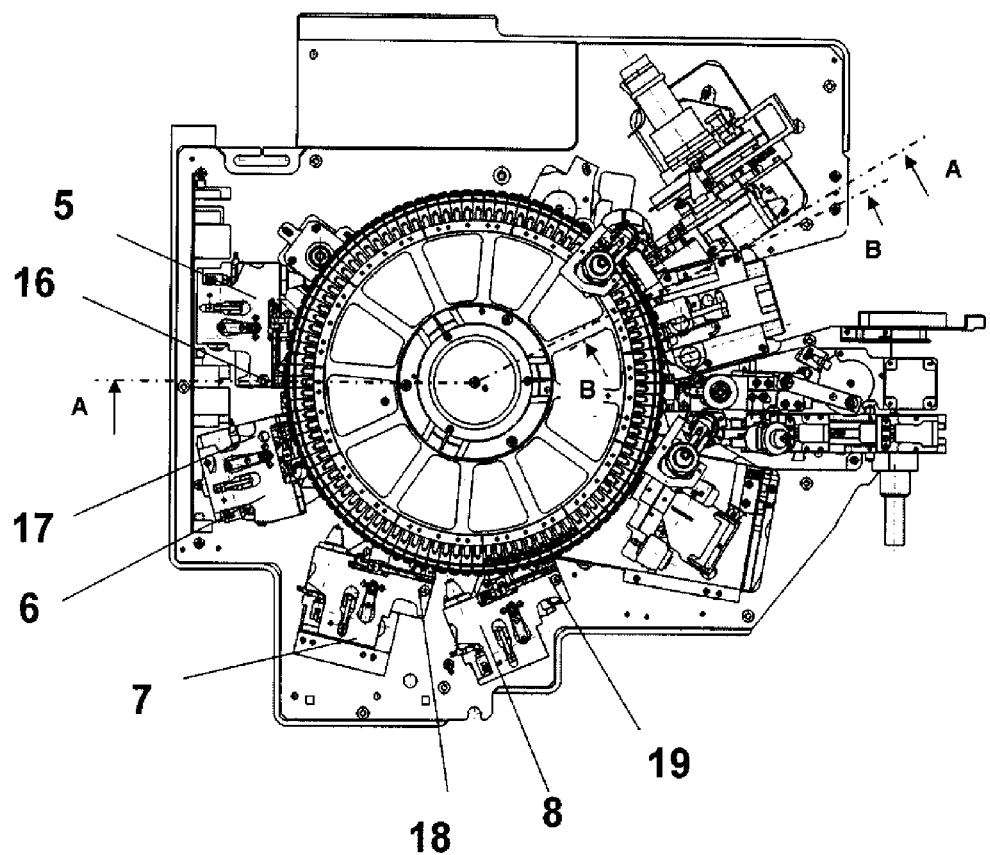
FIG. 3 shows a top plan view of some components of an analyzer according to the invention as represented in FIG. 1.

In another embodiment shown by FIG. 3, a plurality of workstations is arranged around the second cuvette conveyor 12. The plurality of workstations comprises a workstation, e.g. workstation 5 (WSB), 6 (WS2), 7 (WSC1) and/or 8 (WSC2), which is adapted for removing a cuvette 31 from a cuvette holder of the at least second cuvette conveyor 12. The workstation is also adapted for transporting the cuvette 31 to a processing position 16, 17, 18, 19 and, from that processing position, back to a cuvette holder of the at least second cuvette conveyor 12. As shown by FIG. 3, processing positions are defined e.g. by pipetting openings 16, 17, 18, 19 of work stations 5, 6, 7, 8 respectively.

Example 2

Second Illustrated Embodiment of an Analyzer

Figure 16:
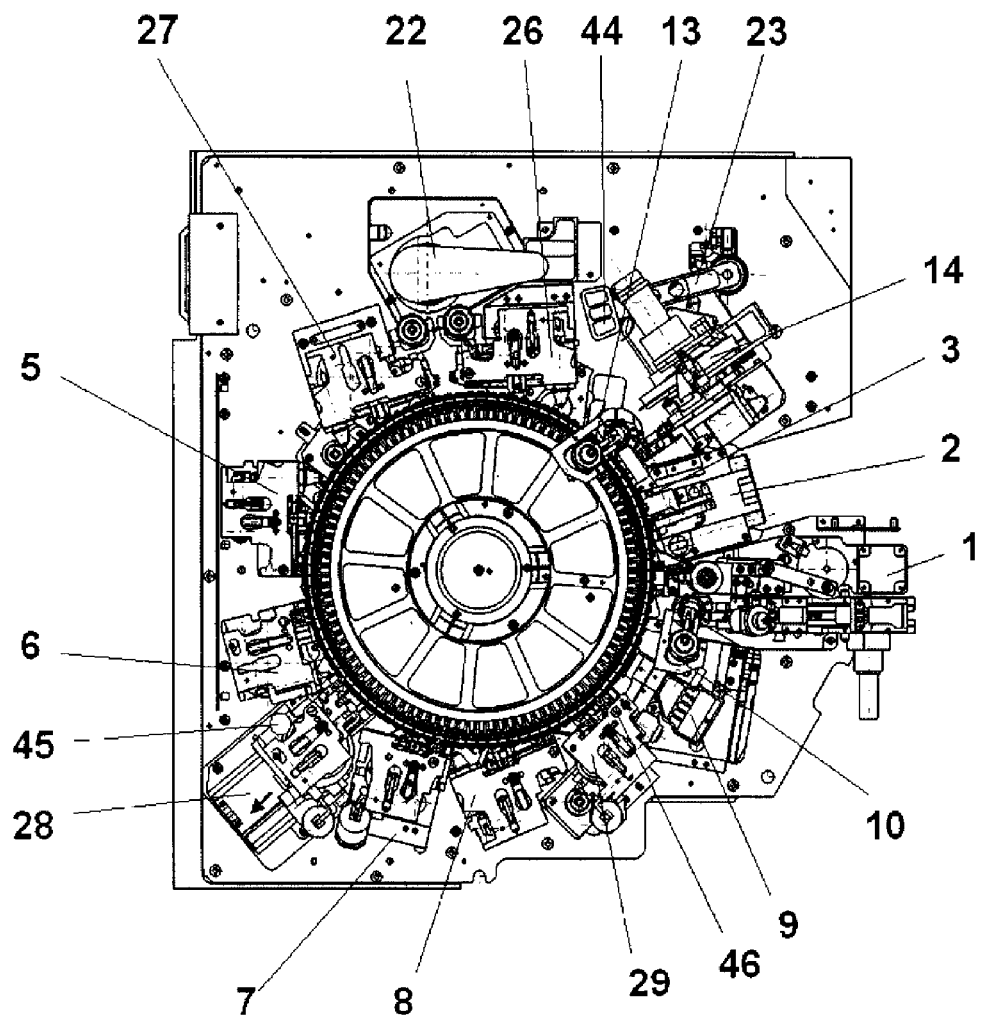
FIG. 16 shows a top plan view of the analyzer according to the invention as represented in FIG. 1 and including workstations suitable for performing immunoassays.
Figure 17:
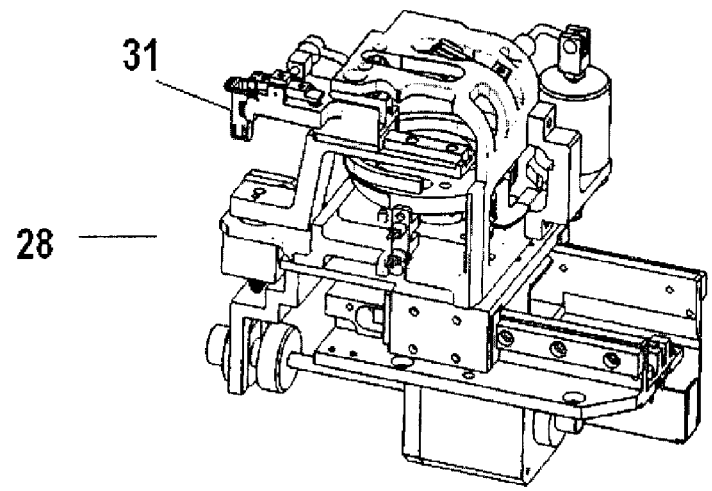
FIG. 17 shows a perspective view of workstation 28 (WSG) represented in FIG. 16.
Figure 18:
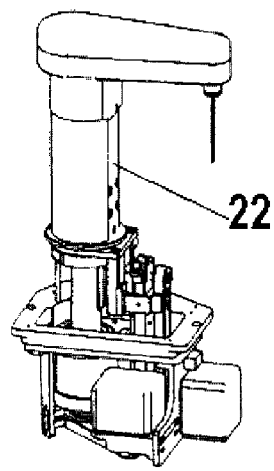
FIG. 18 shows a first perspective view of workstation 22 (WSK) represented in FIG. 16.
Figure 19:
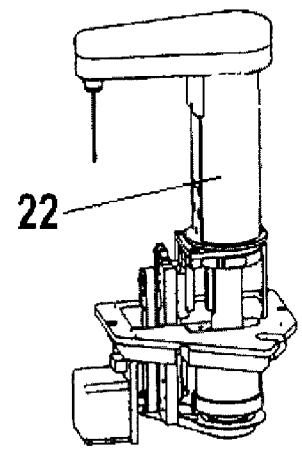
FIG. 19 shows a second perspective view of workstation 22 (WSK) represented in FIG. 16.
Figure 20:
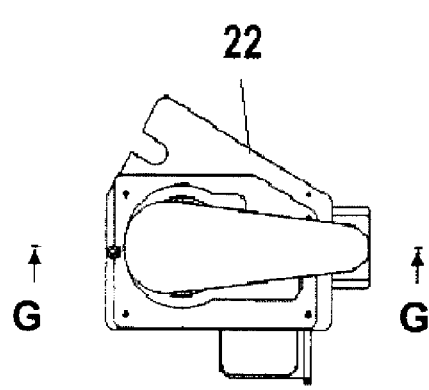
FIG. 20 shows a top view of workstation 22 (WSK) represented in FIG. 16.
Figure 21:
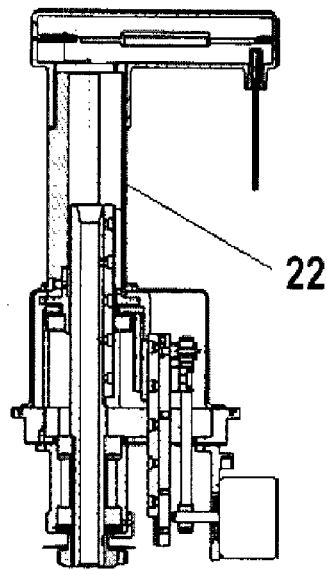
FIG. 21 shows a cross-sectional view of workstation 22 (WSK) taken along plane G-G in FIG. 20.
Figure 22:
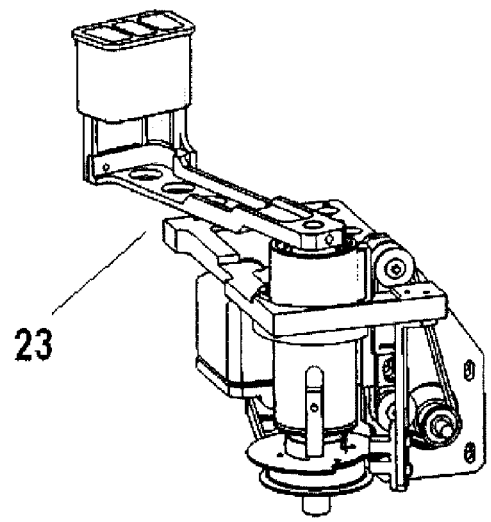
FIG. 22 shows a perspective view of workstation 23 (WSL) represented in FIG. 16.
Figure 23:
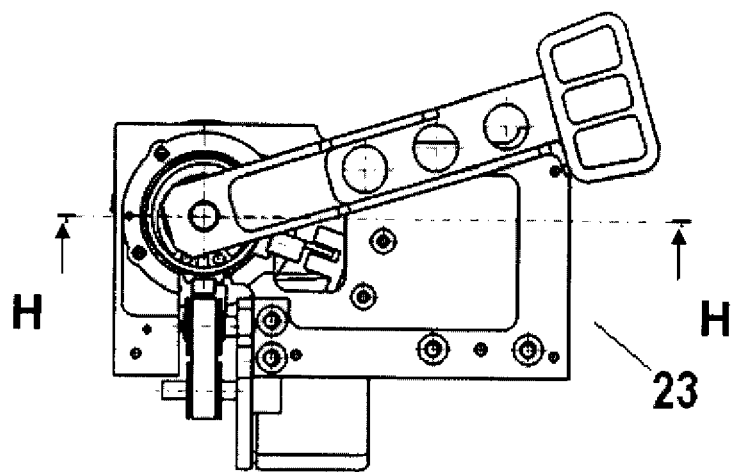
FIG. 23 shows a top view of workstation 23 (WSL) represented in FIG. 16.
Figure 24:
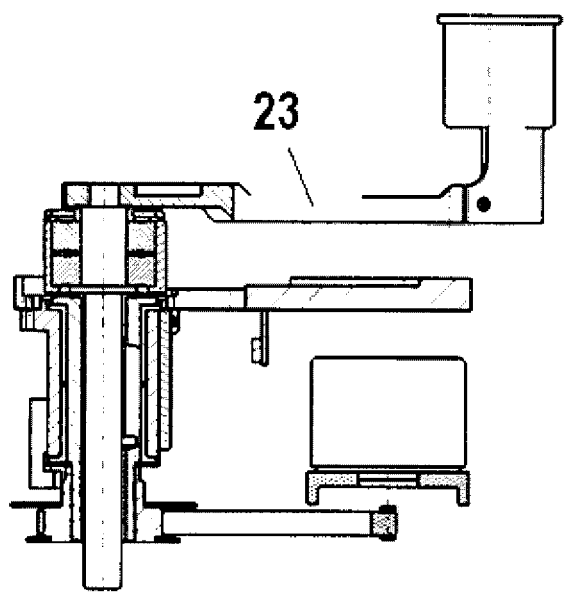
FIG. 24 shows a cross-sectional view of workstation 23 (WSL) represented in FIG. 16 taken along plane H-H in FIG. 23.

A second embodiment of an analyzer according to the invention is shown by FIG. 16. This second embodiment comprises the above-mentioned components of the analyzer described above as Example 1 and the plurality of workstations arranged around the cuvette conveyors. The plurality of workstations comprises: a workstation 22 (WSK) which is shown also by FIGS. 19, 20, 21 and 22, workstation 26 (WSI 1), optionally a workstation 27 (WSI 2) which has the same structure and function as workstation 26 (WSI 1), workstation 28 (WSG) which is shown also by FIG. 17, a workstation 29 (WSH), and a workstation 23 (WSL) which is shown also by FIGS. 23, 24 and 25.

In FIG. 16, the reference numbers 44, 45 and 46 designate a pipetting position in workstation 14 (WSF), workstation 28 (WSG), and workstation 29 (WSH) respectively.

Workstation 22 (WSK) is adapted for taking out liquid from a cuvette 31 and/or adding liquid to a cuvette 31, wherein cuvette 31 in one embodiment is held by workstation 26 (WSI 1). Workstation 26 (WSI 1) is adapted for removing a cuvette 31 from a cuvette holder of the at least second cuvette conveyor 11, for mixing the liquid in the cuvette, and for inserting the cuvette 31 into one of the cuvette holders of the at least second cuvette conveyor 11.

Workstation 28 (WSG) is adapted for removing a cuvette 31 from a cuvette holder of the at least second cuvette conveyor 11, for transporting the cuvette 31 to a reagent pipetting position 45, for mixing the liquid in the cuvette 31, and for transporting the cuvette 31 from that pipetting position to one of the cuvette holders of the at least second cuvette conveyor 11.

Workstation 29 (WSH) is adapted for removing a cuvette 31 from a cuvette holder of the at least second cuvette conveyor 11, for transporting the cuvette 31 to a sample pipetting position 46, for mixing the liquid in the cuvette 31, and for transporting the cuvette 31 from that pipetting position back to one of the cuvette holders of the at least second cuvette conveyor 11.

Workstation 23 (WSL) is a washing station which serves for cleaning the pipetting needle 41 and which provides cleaning liquids for rinsing a measuring station.

In other embodiments of the analyzers according to Example 1 and Example 2, absorption photometer 9 photometrically measures the contents of a cuvette 31 held by one of the cuvette holders.

In other embodiments of the analyzers according to Example 1 and Example 2, the analyzer comprises a fourth cuvette transport device 3 (WSE) for removing a cuvette 31 containing a sample-reagent-mixture from a cuvette holder, and for holding the cuvette 31 at a measurement position for the fluorescence polarization photometer 2. The fourth cuvette transport device 3 also inserts the cuvette 31 into one of the cuvette holders or transfers the cuvette 31 to a cuvette ejection device e.g. waste drop-off station 10, after a measurement of the cuvette contents in the fluorescence polarization photometer 2.

Figure 25:
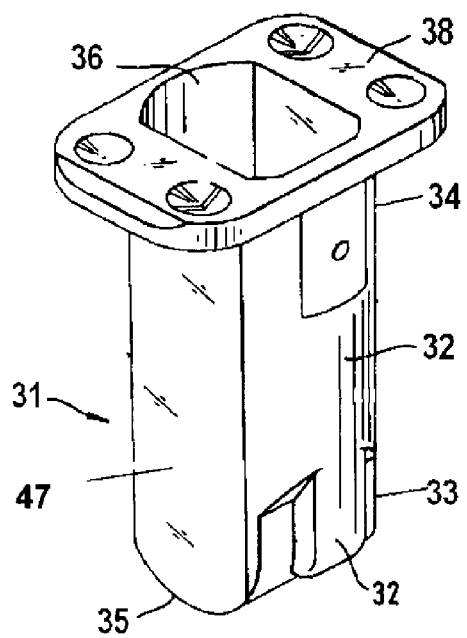
FIG. 25 shows a perspective view of a cuvette 31.
Figure 26:
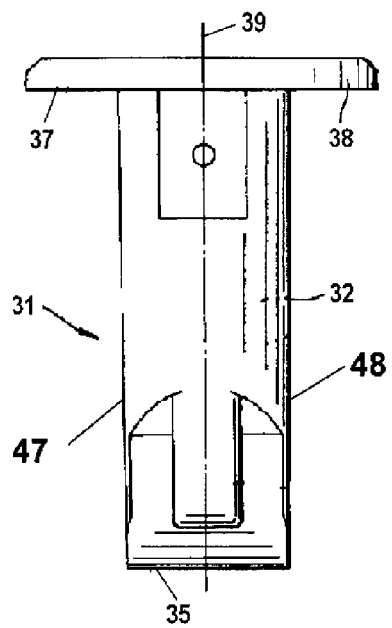
FIG. 26 shows a first side view of cuvette 31 shown by FIG. 25.
Figure 27:
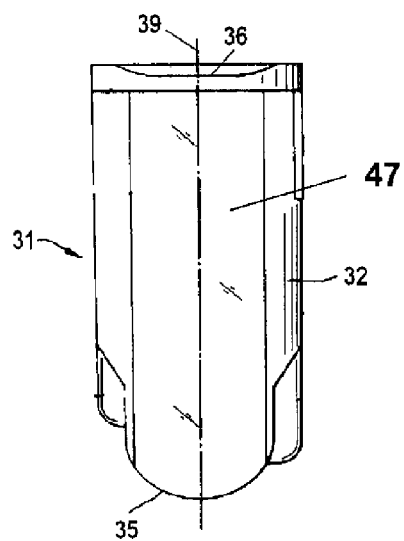
FIG. 27 shows a second side view of cuvette 31 shown by FIG. 25.

In other embodiments of the analyzers according to Example 1 and Example 2, the analyzer further comprises a plurality of reaction cuvettes 31 of the type illustrated by FIGS. 25, 26 and 27. Each cuvette 31 is insertable into one of the cuvette holders of the cuvette conveyors 11 and 12. Cuvette 31 has a tubular body 32 which has a longitudinal axis 39 and two opposite ends along said longitudinal axis. The tubular body 32 has an upper opening 36, a bottom wall 35, planar side walls 47, 48 opposing each other through which optical detection is carried out, and tongues 37, 38 which are adjacent to the upper opening 36 and which extend in opposite directions along a plane normal to the longitudinal axis 39. Each of the tongues 37, 38 is insertable in one of the cuvette holders of the cuvette conveyors 11 and 12. Planar side walls 47, 48 are in one embodiment plane-parallel side walls which are parallel to each other.

FIGS. 28 to 44 illustrate the cooperation of the various workstations with the cuvette conveyors 11 and 12 and with the photometers 2 and 9.

Figure 28:
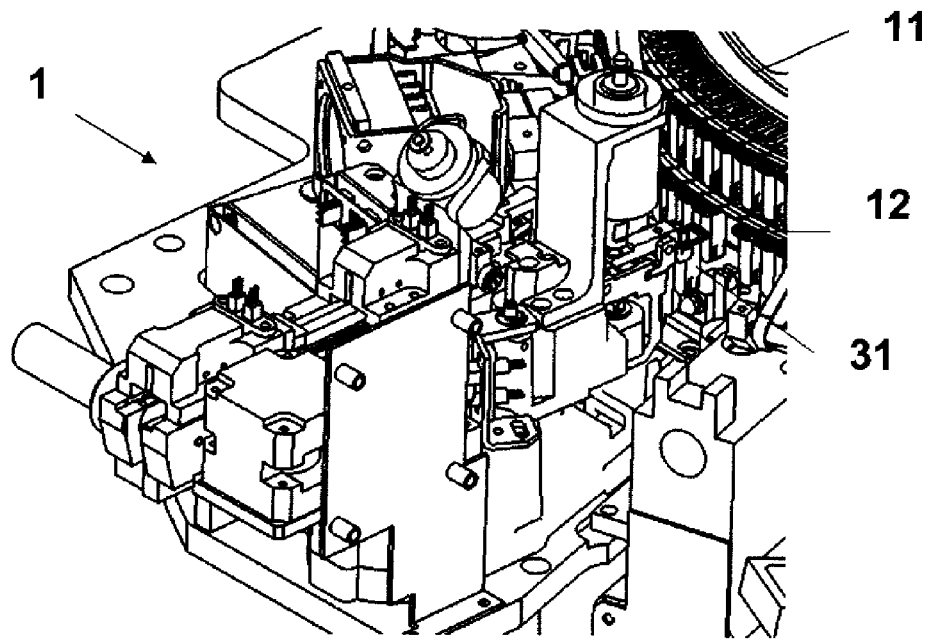
FIG. 28 shows a partial perspective view of workstation 1 (WSA) and conveyors 11 and 12 shown in FIG. 1.

FIG. 28 shows workstation 1 (WSA) as a gripper thereof takes a cuvette 31 from a cuvette holder of conveyor 12.

Figure 29:
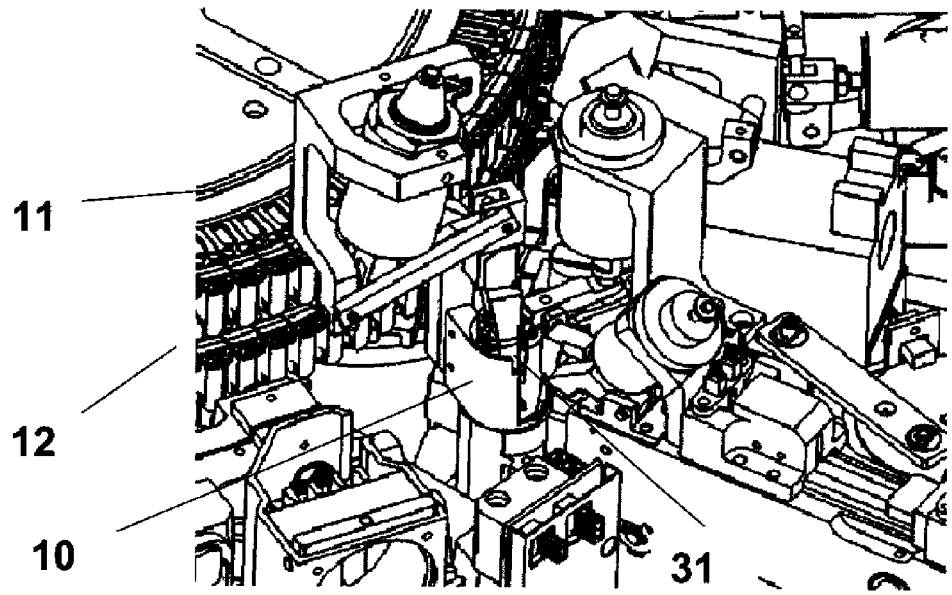
FIG. 29 shows a partial perspective view of workstation 1 (WSA), drop-off station 10 and conveyors 11 and 12 in FIG. 1.

FIG. 29 shows workstation 1 (WSA) as a gripper thereof delivers a cuvette 31 to drop-off station 10.

Figure 30:
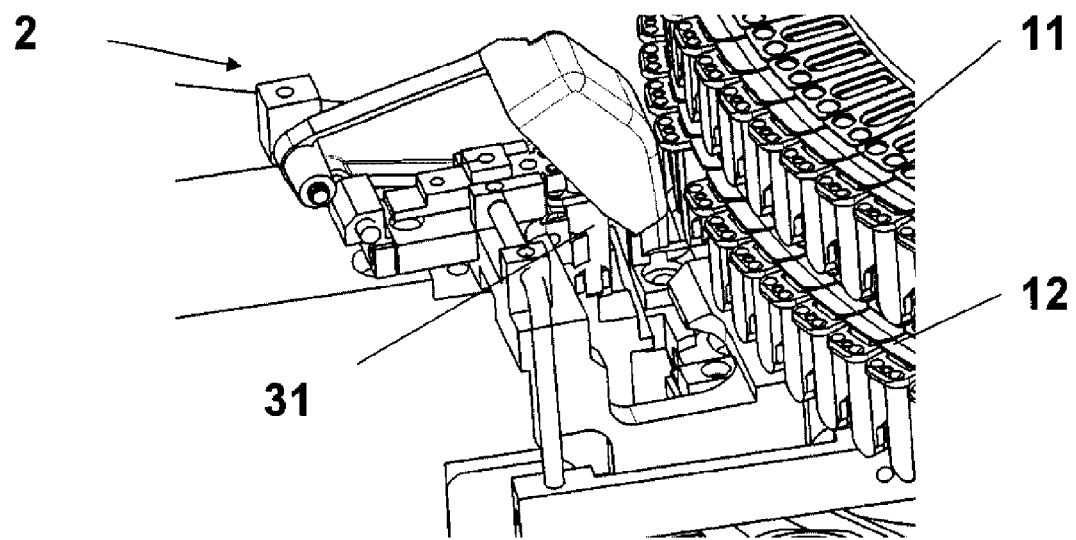
FIG. 30 shows a partial perspective view of fluorescence polarization photometer 2 and conveyors 11 and 12 shown in FIG. 1.

FIG. 30 shows a fluorescence polarization photometer 2 and a cuvette 31 positioned to be measured therewith.

Figure 31:
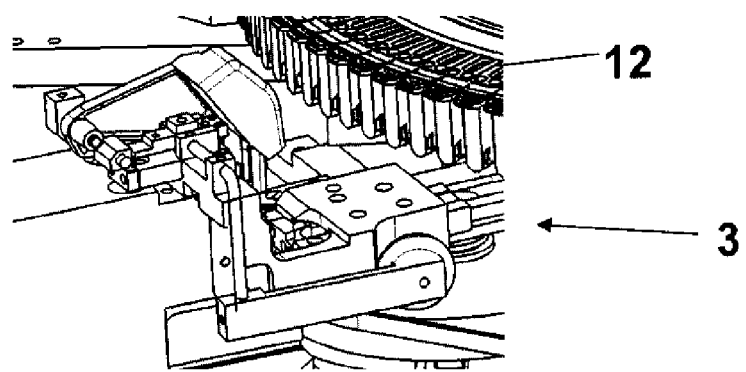
FIG. 31 shows a partial perspective view of workstation 3 (WSE) and conveyor 12 shown in FIG. 1.

FIG. 31 shows workstation 3 (WSE) which serves for taking a cuvette 31 from conveyor 12 and bringing it to a measurement position where the cuvette contents is measured by fluorescence polarization photometer 2.

Figure 32:
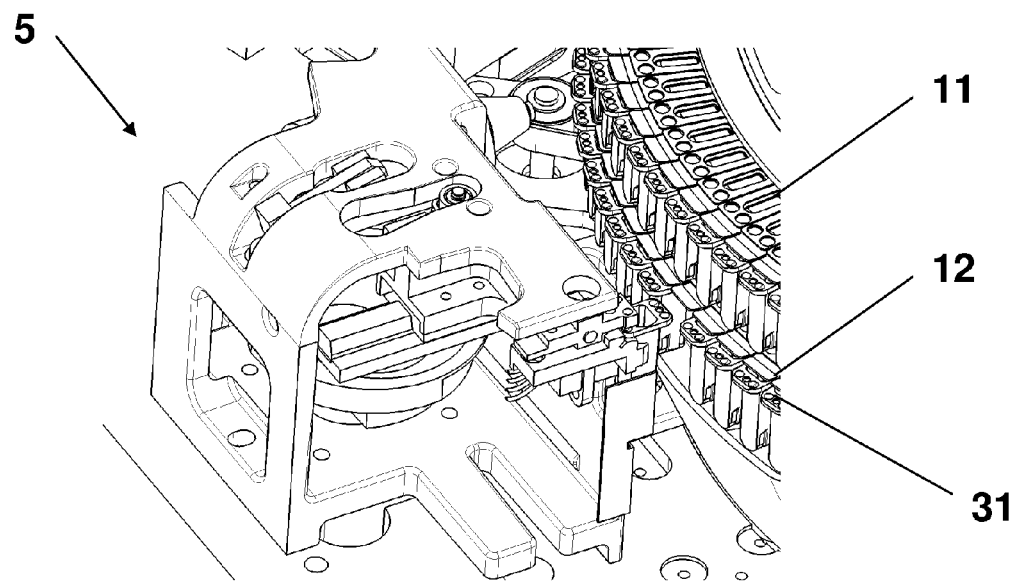
FIG. 32 shows a partial perspective view of workstation 5 (WSB) and conveyors 11 and 12 shown in FIG. 1.

FIG. 32 shows workstation 5 (WSB) as a gripper thereof takes a cuvette 31 from a cuvette holder of conveyor 12.

Figure 33:
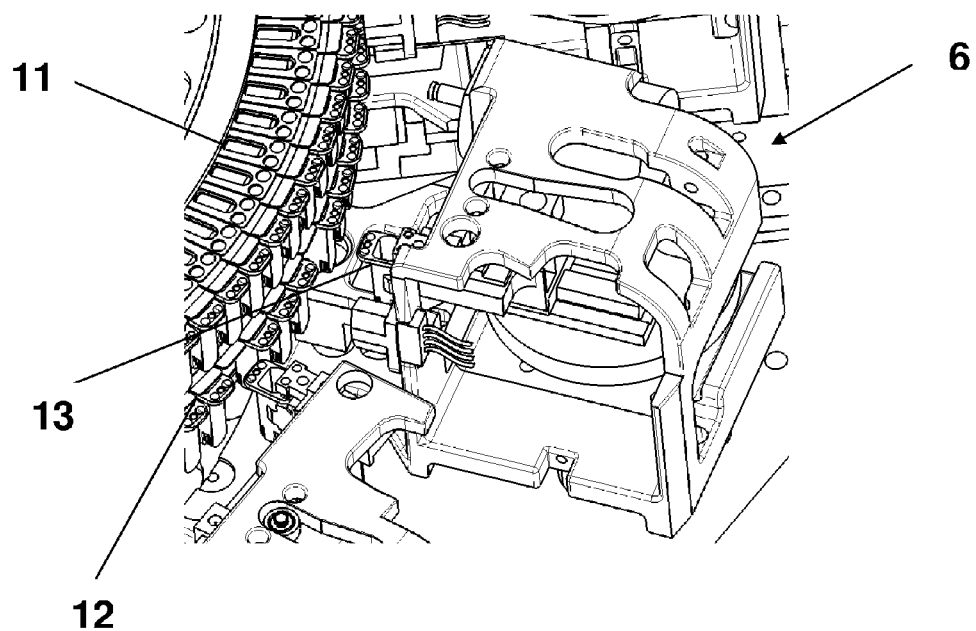
FIG. 33 shows a partial perspective view of workstation 6 (WS2) and conveyors 11 and 12 shown in FIG. 1.

FIG. 33 shows workstation 6 (WS2) as a gripper thereof takes a cuvette 31 from a cuvette holder of conveyor 12.

Figure 34:
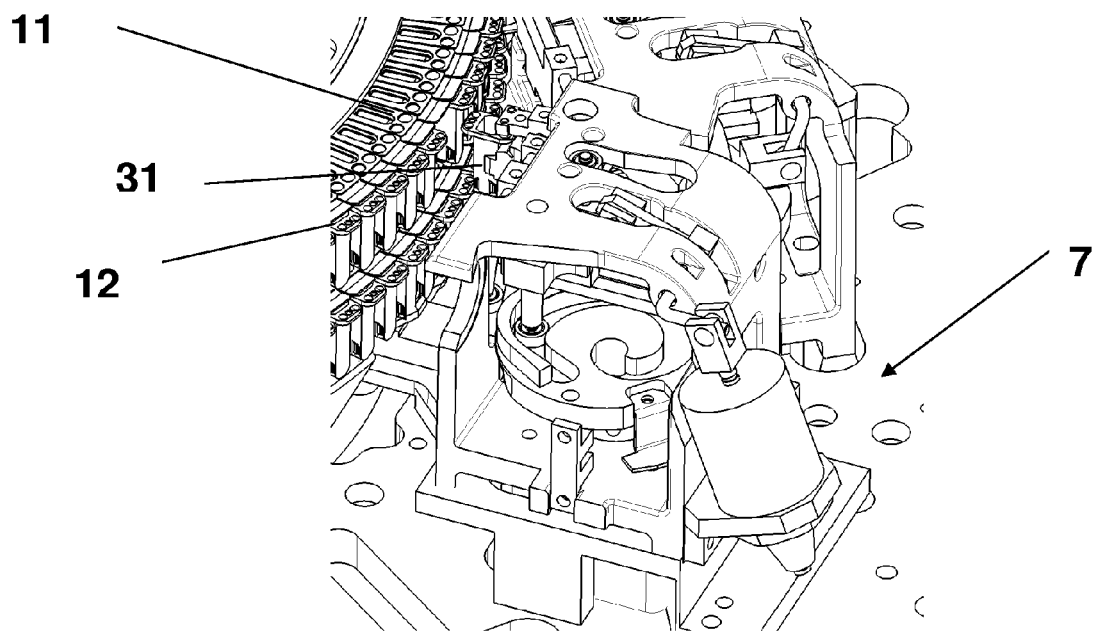
FIG. 34 shows a partial perspective view of workstation 7 (WSC1) and conveyors 11 and 12 shown in FIG. 1.

FIG. 34 shows workstation 7 (WSC1) as a gripper thereof takes a cuvette 31 from a cuvette holder of conveyor 11.

Figure 35:
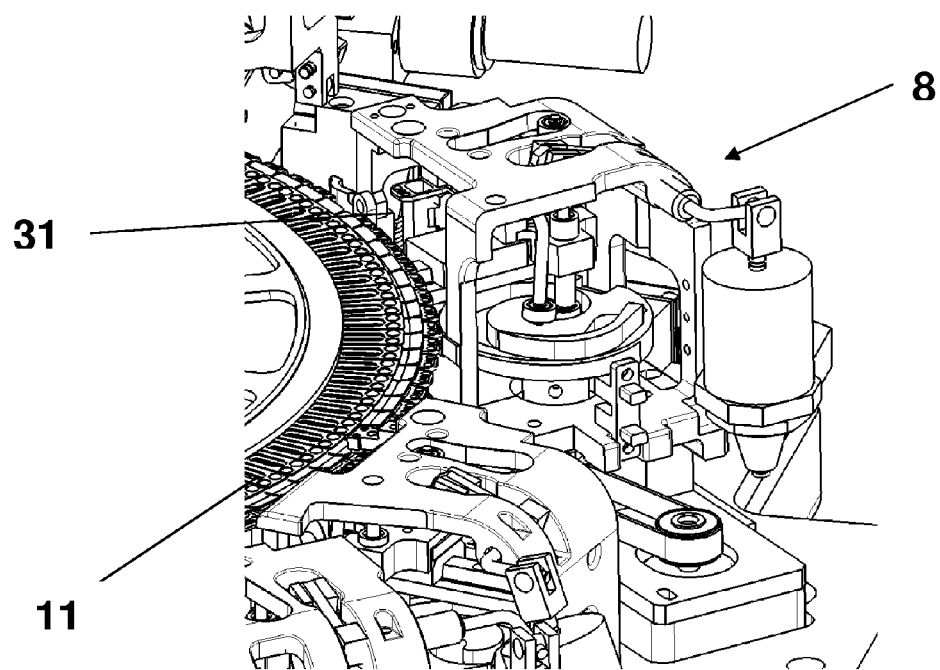
FIG. 35 shows a partial perspective view of workstation 7 (WSC2) and conveyor 11 shown in FIG. 1.

FIG. 35 shows workstation 8 (WSC2) as a gripper thereof takes a cuvette 31 from a cuvette holder of conveyor 11.

Figure 36:
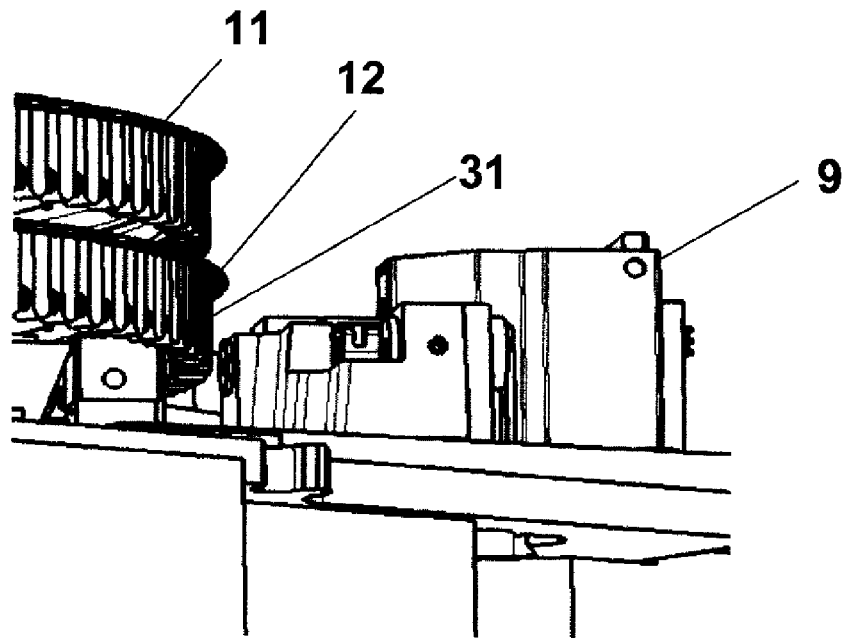
FIG. 36 shows a partial perspective view of absorptions photometer 9 and conveyors 11 and 12 shown in FIG. 1.

FIG. 36 shows absorptions photometer 9 as it measures the contents of one of the cuvettes 31 held by conveyor 12 as the cuvette passes in front of photometer 9 during rotation of conveyor 12.

Figure 37:
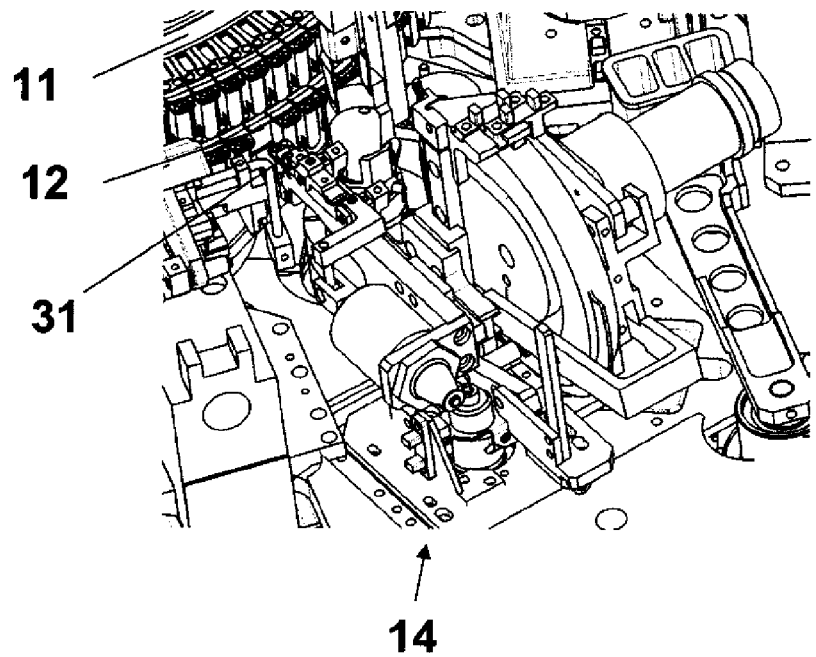
FIG. 37 shows a first partial perspective view of workstation 14 (WSF) and conveyors 11 and 12 shown in FIG. 1.

FIG. 37 shows workstation 14 (WSF) as a gripper thereof takes a cuvette 31 from a cuvette holder of conveyor 12.

Figure 38:
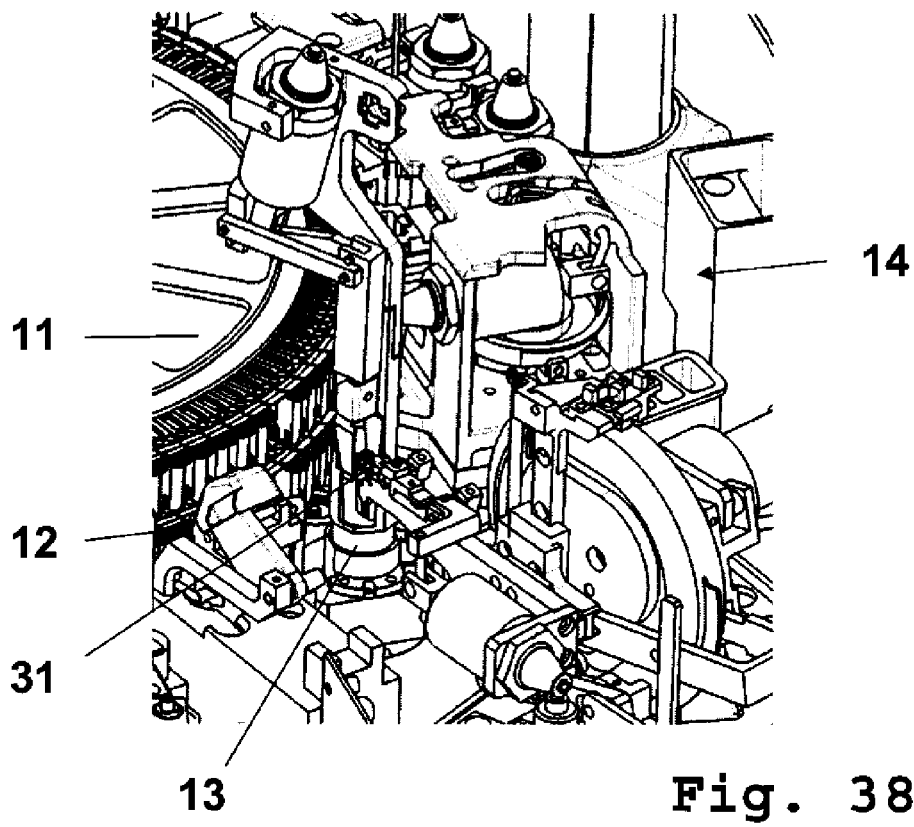
FIG. 38 shows a second partial perspective view of workstation 14 (WSF) shown in FIG. 16 and of conveyors 11 and 12 shown in FIG. 1.

FIG. 38 shows workstation 14 (WSF) as a gripper thereof delivers a cuvette 31 to drop-off station 13.

Figure 39:
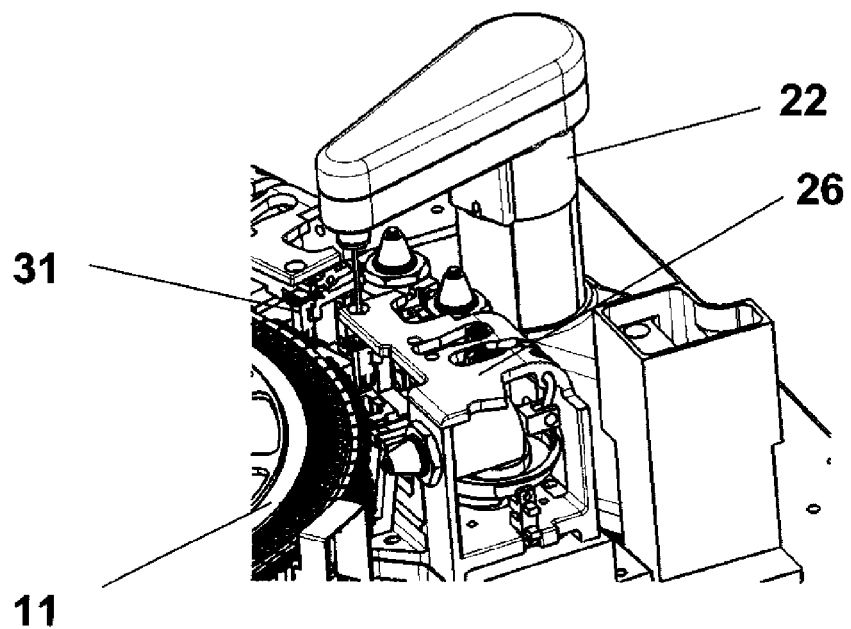
FIG. 39 shows a partial perspective view of workstation 22 (WSK) and conveyor 11 shown in FIG. 16.

FIG. 39 shows workstation 22 (WSK) effecting a pipetting operation on a cuvette 31 positioned in workstation 26 (WSI 1).

Figure 40:
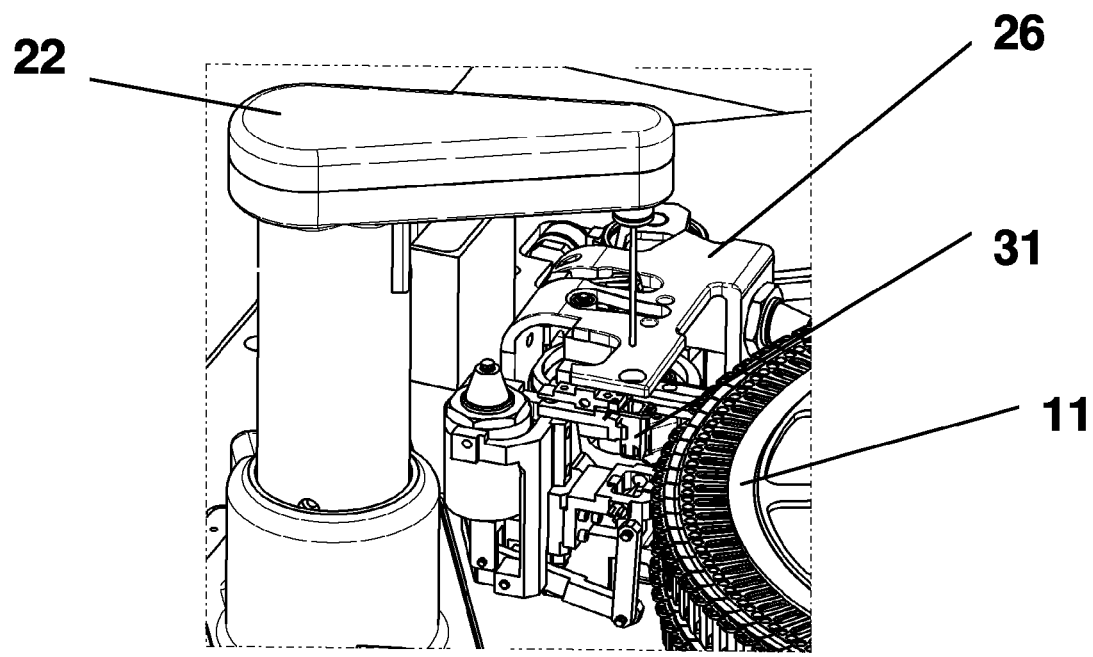
FIG. 40 shows a partial perspective view of workstation 26 (WSI 1) shown in FIG. 16 and of conveyors 11 and 12 shown in FIG. 1.

FIG. 40 shows workstation 26 (WSI 1) holding a cuvette 31 removed by workstation 26 (WSI 1) from a cuvette holder of cuvette conveyor 11.

Figure 41:
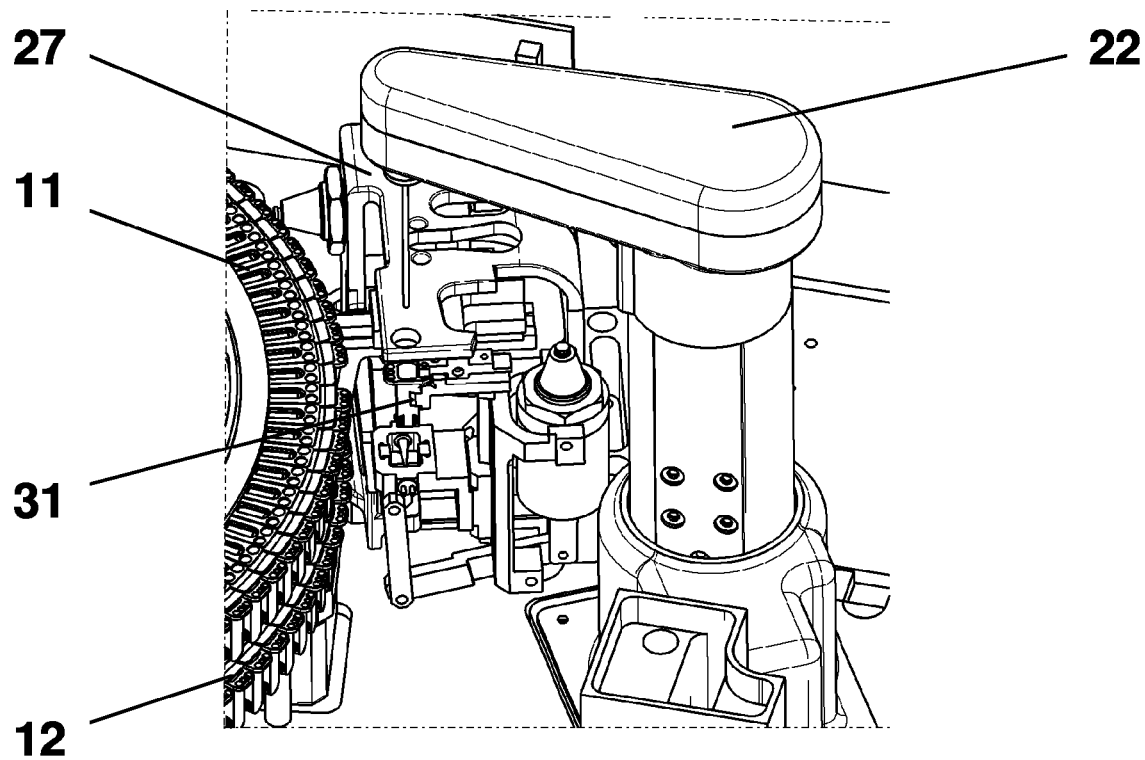
FIG. 41 shows a partial perspective view of workstation 27 (WSI 2) shown in FIG. 16 and of conveyors 11 and 12 shown in FIG. 1.

FIG. 41 shows workstation 27 (WSI 2) holding a cuvette 31 removed by workstation 26 (WSI 2) from a cuvette holder of cuvette conveyor 11.

Figure 42:
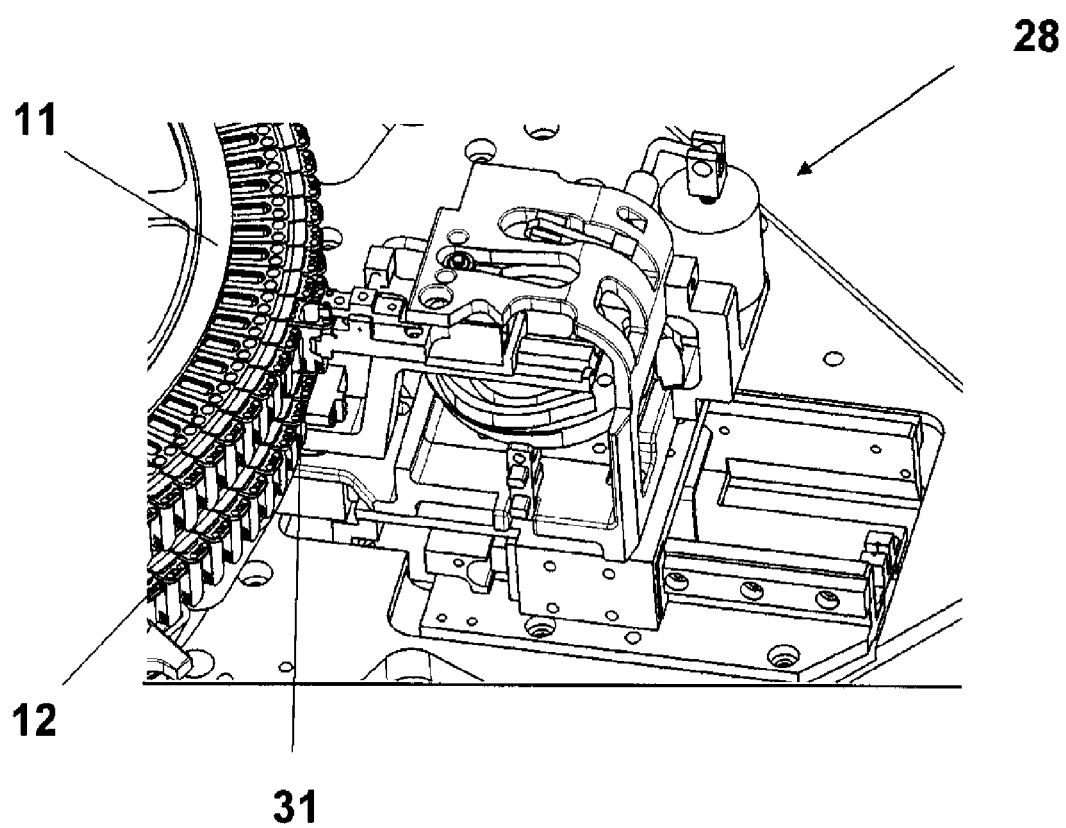
FIG. 42 shows a first partial perspective view of workstation 28 (WSG) shown in FIG. 16 and of conveyors 11 and 12 shown in FIG. 1.

FIG. 42 shows workstation 28 (WSG) holding a cuvette 31 being removed from or inserted into a cuvette holder of cuvette conveyor 11.

Figure 43:
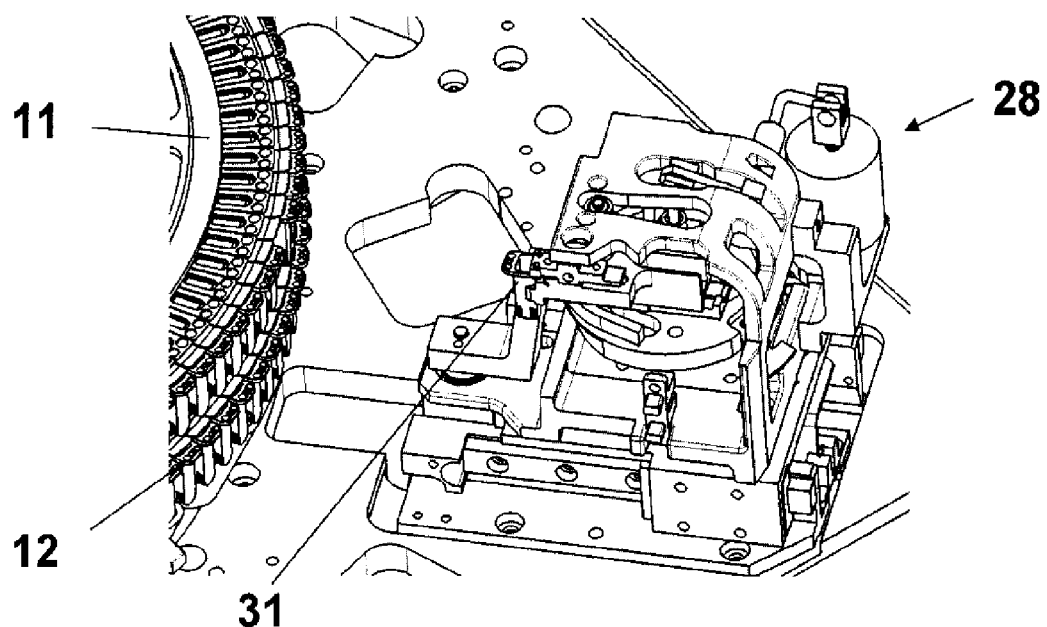
FIG. 43 shows a second partial perspective view of workstation 28 (WSG) shown in FIG. 16 and of conveyors 11 and 12 shown in FIG. 1.

FIG. 43 shows workstation 28 (WSG) holding a cuvette 31 and being ready for a pipetting operation that is to be effected on the cuvette 31.

Figure 44:
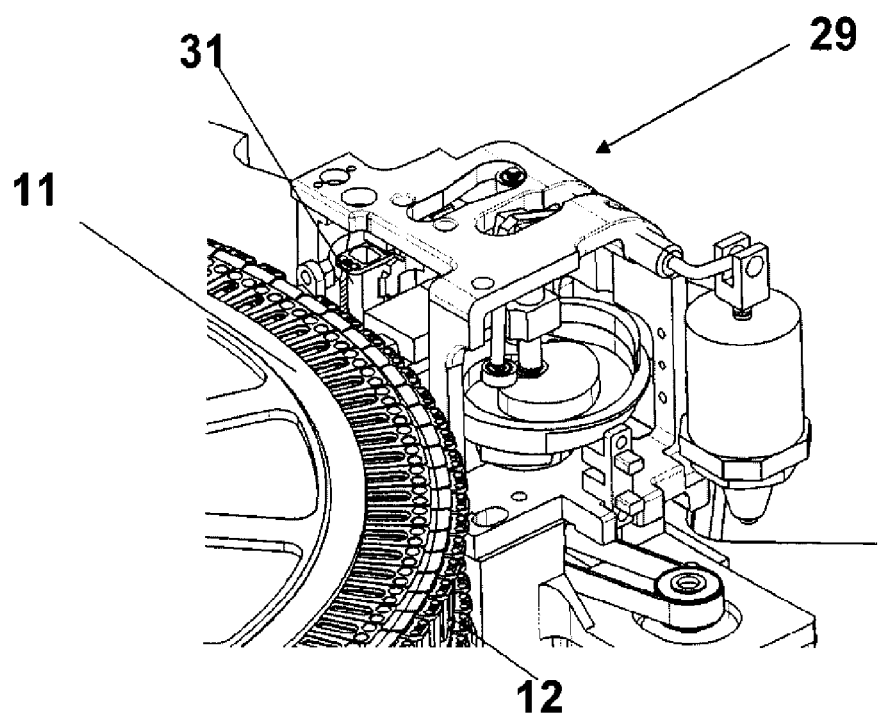
FIG. 44 shows a partial perspective view of workstation 29 (WSH) shown in FIG. 16 and of conveyors 11 and 12 shown in FIG. 1.

FIG. 44 shows workstation 29 (WSH) holding a cuvette 31 removed by workstation 29 (WSH) from a cuvette holder of cuvette conveyor 11.

What is claimed is:

1. An analyzer for performing medical diagnostic analysis of biological samples, said analyzer comprising:
a first disk-shaped cuvette conveyor having a first array of cuvette holders spaced along a first circle;
a first drive unit which rotates said first cuvette conveyor about a rotation axis in order to position cuvettes carried by the first cuvette conveyor at a first angular position;
at least a second disk-shaped cuvette conveyor having a second array of cuvette holders spaced along a second circle,
said cuvette holders of said first cuvette conveyor and said cuvette holders of said at least second cuvette conveyor hold cuvettes having the same shape and dimensions,
the centers of said first circle and said second circle lying on a vertical axis which is a common rotation axis of said first cuvette conveyor and said at least second cuvette conveyor,
said first cuvette conveyor and said at least second cuvette conveyor being rotatable around said common rotation axis,
said first array of cuvette holders and said second array of cuvette holders being spaced from each other in axial direction along said rotation axis with an air gap between said first array of cuvette holders and said second array of cuvette holders and in which said first array of cuvette holders and said second array of cuvette holders are aligned directly on top of one another;
at least a second drive unit which rotates said at least second cuvette conveyor about said vertical rotation axis in order to position cuvettes carried by the at least second cuvette conveyor at a second angular position, the operation of said at least second drive unit being independent from the operation of said first drive unit, and
at least one of an absorption photometer and a fluorescence polarization photometer which photometrically measures the content of a cuvette;
a first cuvette transport device which is located close to a periphery of both said first cuvette conveyor and said at least said second cuvette conveyor, and which transports a cuvette from one of the cuvette holders of said first cuvette conveyor to one of the cuvette holders of said at least second cuvette conveyor and/or vice versa;
a housing which defines a chamber within which air temperature is regulated and maintained at a determined value, said first cuvette conveyor and said at least second cuvette conveyor being located within said chamber; and
a plurality of workstations arranged around and close to the periphery of said first cuvette conveyor and said at least second cuvette conveyor, said workstations comprising a cuvette transport device which removes a cuvette from one of said cuvette holders of said first cuvette conveyor or of said at least second cuvette conveyor, and transports the cuvette to a processing position and from said processing position to one of said cuvette holders of said first cuvette conveyor or of said at least second cuvette conveyor.

2. An analyzer according to claim 1, further comprising a plurality of reaction cuvettes, each of which is insertable into one of said cuvette holders of said cuvette conveyors, each of said cuvettes having a tubular body having a longitudinal axis and two opposite ends along said longitudinal axis, said tubular body having an upper opening, a bottom wall, and planar side walls opposite to each other through which optical detection is carried out, said tubular body having tongues which are adjacent to said upper opening and which extend in opposite directions along a plane normal to said longitudinal axis, each of said tongues being insertable in one of said cuvette holders.

3. An analyzer according to claim 1, wherein said first cuvette transport device further removes the cuvette from one of the cuvette holders of said at least second cuvette conveyor and transfers said cuvette to a cuvette ejection device.

4. An analyzer according to claim 1, wherein said first cuvette transport device further transfers said cuvette from one of the cuvette holders of said at least second cuvette conveyor to a processing position and from said processing position back to said cuvette holder, or to a cuvette ejection device.

5. An analyzer according to claim 1, further comprising an automatic pipetting unit which pipettes a sample or a reagent aliquot into a selected cuvette at a selected processing position at a selected point of time, the location of said processing position being associated with the position of one of said plurality of workstations.

6. An analyzer according to claim 5, further comprising a control unit which controls the operation of said first drive unit, said at least second drive unit, said cuvette transport device, said plurality of workstations and said automatic pipetting unit.

7. An analyzer according to claim 1, wherein said at least second cuvette conveyor has the same shape and dimensions as said first cuvette conveyor.

8. An analyzer according to claim 1, wherein each of said cuvette holders has a recess for receiving a tongue which is an integral portion of a cuvette, said recess extending in radial direction and said tongue being insertable in said recess in radial direction.

9. An analyzer according to claim 1, which further comprises a second cuvette transport device (WSA) which performs automatically at least one of loading empty cuvettes onto said first cuvette conveyor or into said second cuvette conveyor, by inserting each cuvette into a cuvette holder of said first cuvette conveyor or said second cuvette conveyor, respectively, removing a cuvette from one of the cuvette holders of said first cuvette conveyor or from said second cuvette conveyor, and transferring said cuvette to a cuvette ejection device.

10. An analyzer according to claim 1, which further comprises a third cuvette transport device (WSA) which performs automatically at least one of loading empty cuvettes onto said at least second cuvette conveyor, by inserting each cuvette into a cuvette holder of said at least second cuvette conveyor, removing a cuvette from one of the cuvette holders of said at least second cuvette conveyor, and transferring said cuvette to a cuvette ejection device.

11. An analyzer according to claim 1, further comprising:
a workstation (WSK) which performs at least one of taking out liquid from a cuvette held by a workstation (WSI 1) and adding liquid to the cuvette,
a workstation (WSG), which removes the same or a different cuvette from a cuvette holder of said at least second cuvette conveyor, transports said cuvette to a reagent pipetting position, mixes the liquid in said cuvette, and transports said cuvette from the pipetting position to one of said cuvette holders, and
a workstation (WSH), which removes the same or a different cuvette from a cuvette holder of said at least second cuvette conveyor, transports said cuvette to a sample pipetting position, mixes the liquid in said cuvette, and transports said cuvette from the pipetting position to one of said cuvette holders.

12. An analyzer according to claim 2, wherein said cuvettes have an inner volume in a range going from 0.2 to 3 milliliter.

\* \* \* \* \*

UNITED STATES PATENT AND TRADEMARK OFFICE
CERTIFICATE OF CORRECTION

PATENT NO. : 8,431,079 B2  
APPLICATION NO. : 12/956303  
DATED : April 30, 2013  
INVENTOR(S) : Burkard Rosenberg et al.

Page 1 of 1

It is certified that error appears in the above-identified patent and that said Letters Patent is hereby corrected as shown below:

In the Specification

Col. 7, Lines 9-10, "device (WSF)" should read --device 14 (WSF)--;

In the Claims

Col. 10, Claim 1, Line 37, "unit, and" should read --unit;--.

Signed and Sealed this
Seventeenth Day of December, 2013

Margaret A. Focarino
*Commissioner for Patents of the United States Patent and Trademark Office*